United States Patent
Hu et al.

(10) Patent No.: US 10,421,817 B1
(45) Date of Patent: Sep. 24, 2019

(54) ANTIBODIES BINDING HUMAN CLAUDIN 18.2 AND USES THEREOF

(71) Applicant: Beijing Mabworks Biotech Co.Ltd, Beijing (CN)

(72) Inventors: Wenqi Hu, Las Vegas, NV (US); Jiangmei Li, Beijing (CN); Xia Wang, Beijing (CN); Feng Li, Beijing (CN)

(73) Assignee: BEIJING MABWORKS BIOTECH CO., LTD., Beijing (CN)

( * ) Notice: Subject to any disclaimer, the term of this patent is extended or adjusted under 35 U.S.C. 154(b) by 0 days.

(21) Appl. No.: 16/254,587

(22) Filed: Jan. 22, 2019

(30) Foreign Application Priority Data

Jan. 17, 2019 (CN) .......................... 2009 1 0043626

(51) Int. Cl.
| | |
|---|---|
| *A61K 39/395* | (2006.01) |
| *C07K 16/28* | (2006.01) |
| *A61K 47/68* | (2017.01) |
| *A61K 31/704* | (2006.01) |
| *A61K 31/7115* | (2006.01) |
| *A61K 31/282* | (2006.01) |

(52) U.S. Cl.
CPC ........ *C07K 16/2878* (2013.01); *A61K 31/282* (2013.01); *A61K 31/704* (2013.01); *A61K 31/7115* (2013.01); *A61K 47/6801* (2017.08)

(58) Field of Classification Search
None
See application file for complete search history.

(56) References Cited

U.S. PATENT DOCUMENTS

| | | | |
|---|---|---|---|
| 10,017,564 B2 * | 7/2018 | Sahin ................ | A61K 51/1063 |
| 10,174,104 B2 * | 1/2019 | Sahin ................ | A61K 51/1063 |
| 2016/0008465 A1 | 1/2016 | Sahin et al. | |

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Furuse et al., (1998) Claudin-1 and -2: Novel Integral Membrane Proteins Localizing at Tight Junctions with No Sequence Similarity to Occludin.J Cell Biol 141(7) 1539-1550.
Scott et al., (2012) Antibody therapy of cancer. Nature Reviews Cancer. 12 (4):278-287.
Korneev et al., (2017) TLR-signaling and proinflammatory cytokines as drivers of tumorigenesis. Cytokine. 89, 127-135.
GBD 2015 Disease and Injury Incidence and Prevalence Collaborators. Global, regional, and national incidence, prevalence, and years lived with disability for 310 diseases and injuries, 1990-2015: a systematic analysis for the Global Burden of Disease Study 2015, Lancet 388 (10053)1545-1602.
Micke et al., (2014) Aberrantly activated claudin 6 and 18.2 as potential therapy targets in non-small-cell lung cancer, Int J Cancer 135(9)2206-2214.
Niimi et al., (2001) claudin-18, a novel downstream target gene for the T/EBP/NKX2.1 homeodomain transcription factor, encodes lung- and stomach-specific isoforms through alternative splicing, Mol Cell Biol, 21(21) 7380-7390.
Sahin et al., (2016) A phase I dose-escalation study of IMAB362 (Zolbetuximab) in patients with advanced gastric and gastro-oesophageal junction cancer. Eur J Cancer 10 17-26.
Shimobaba et al., (2016) Claudin-18 inhibits cell proliferation and motility mediated by inhibition of phosphorylation of PDK1 and Akt in human lung adenocarcinoma A549 cells, Biochim Biophys Acta 1863(6 Pt A) 1170-1178.
Singh et al., (2017) Anti-claudin 18.2 antibody as new targeted therapy for advanced gastric cancer, J Hematol Oncol 10(1) 105.
Swisshelm et al., (2005) Role of claudins in tumorigenesis, Adv Drug Deliv Rev 57(6) 919-928.
Tanaka et al., (2011) Claudin-18 is an early-stage marker of pancreatic carcinogenesis, J Histochem Cytochem 59(10) 942-952.
Tokumitsu et al., (2016) Immunocytochemistry for Claudin-18 and Maspin in biliary brushing cytology increases the accuracy of diagnosing pancreatobiliary malignnancies. Cytopathology 28(2).

* cited by examiner

*Primary Examiner* — Meera Natarajan
(74) *Attorney, Agent, or Firm* — Kening Li; Duane Morris LLP

(57) ABSTRACT

An isolated monoclonal antibody that specifically binds human Claudin 18.2. A nucleic acid molecule encoding the antibody, an expression vector, a host cell and a method for expressing the antibody are also provided. The present invention further provides an immunoconjugate, a bispecific molecule, a chimeric antigen receptor, an oncolytic virus and a pharmaceutical composition comprising the antibody, as well as a diagnostic or treatment method using an anti-Claudin 18.2 antibody of the invention.

19 Claims, 11 Drawing Sheets

Specification includes a Sequence Listing.

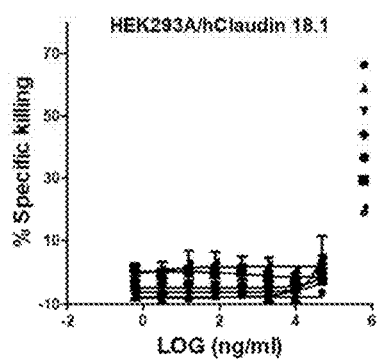 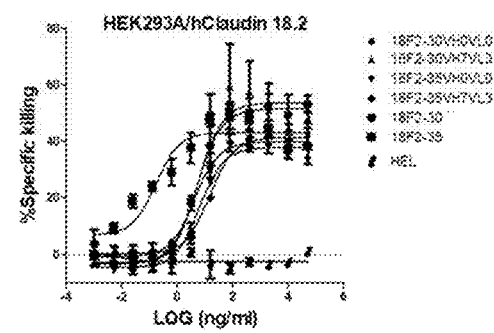
FIG. 11A                FIG. 11B
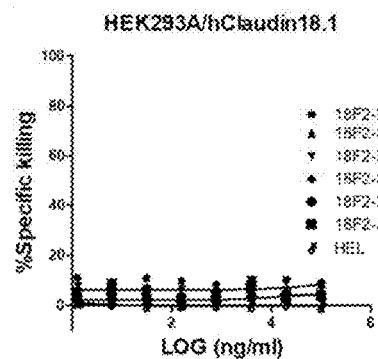 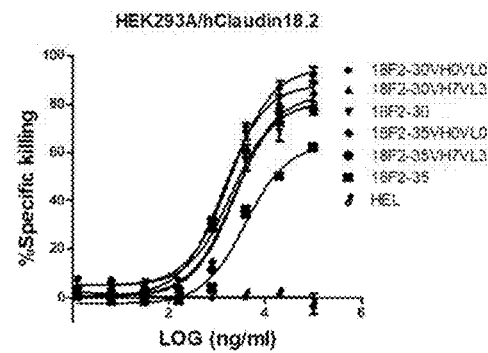
FIG. 12A                FIG. 12B

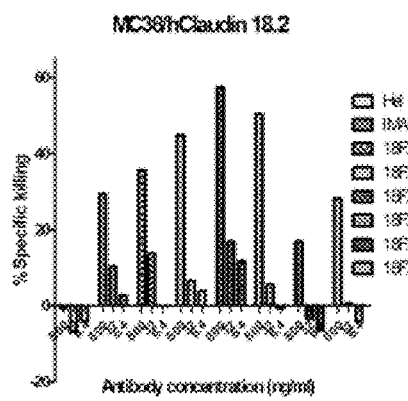 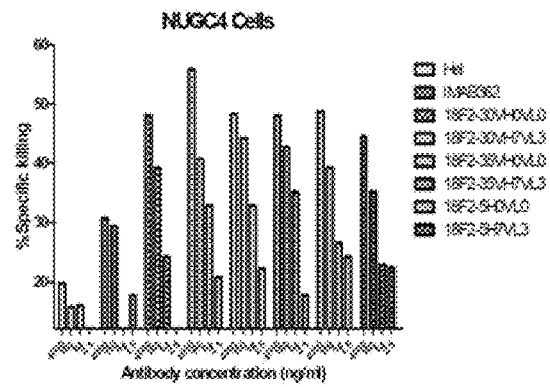
FIG. 17A  FIG. 17B
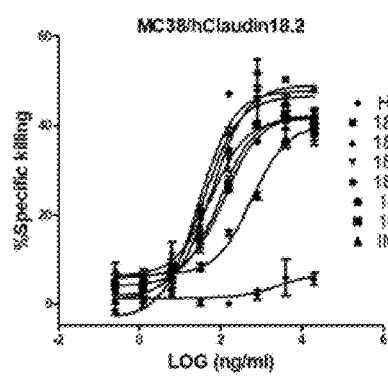 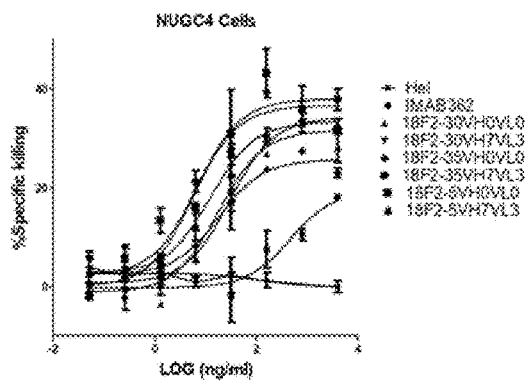
FIG. 18A  FIG. 18B

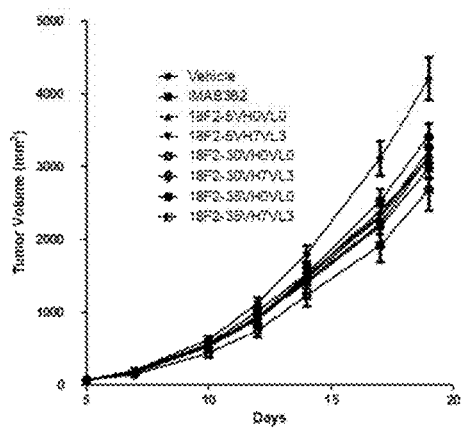 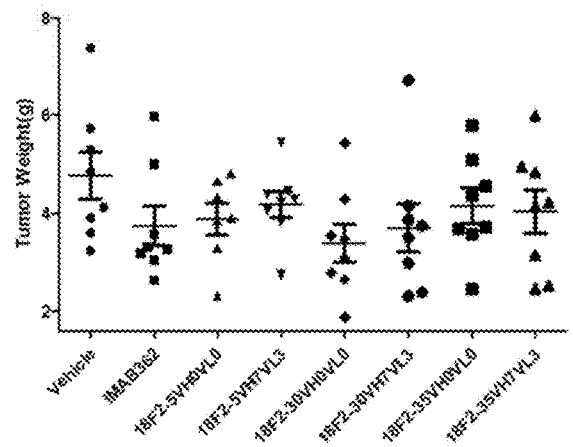
FIG. 19A  FIG. 19B
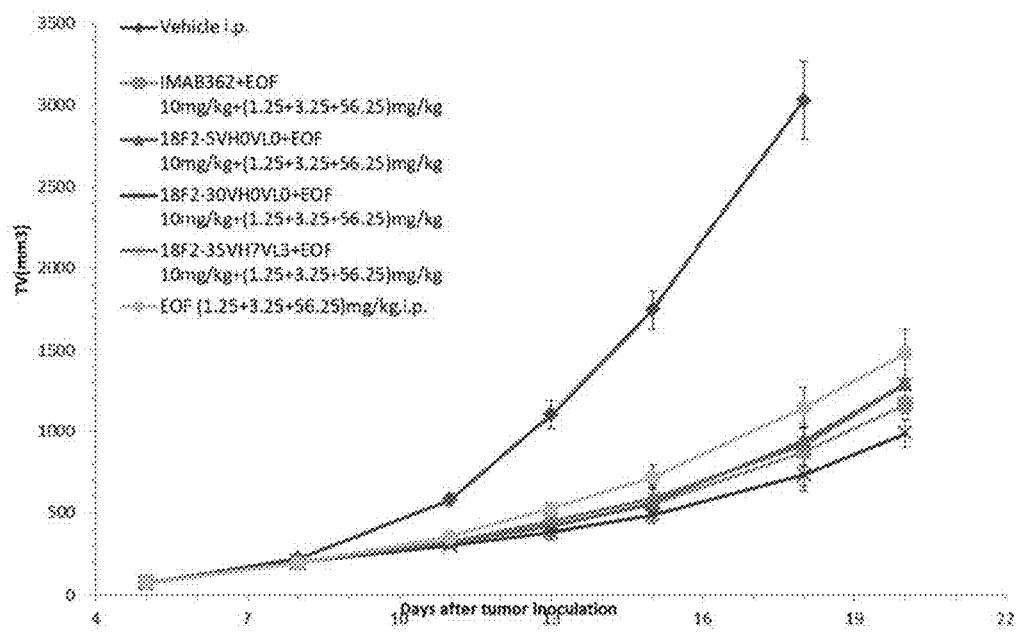
FIG. 20

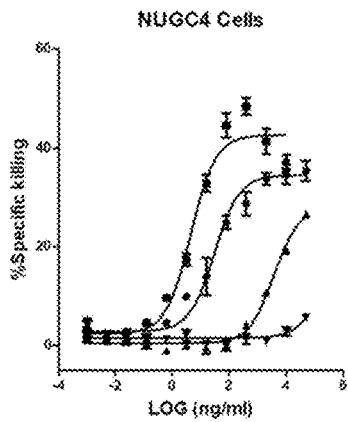
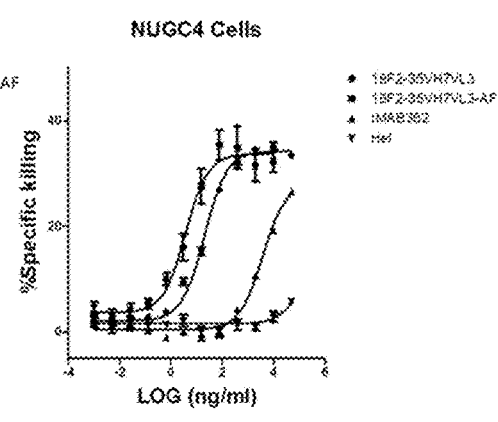
FIG. 21A        FIG. 21B
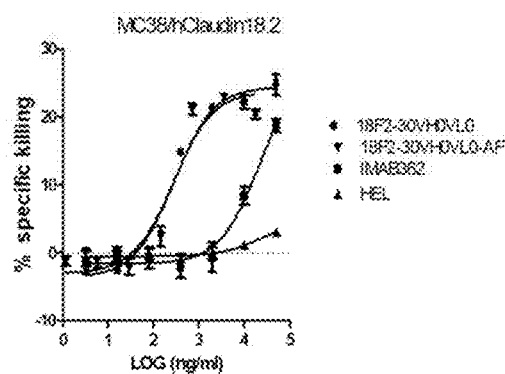
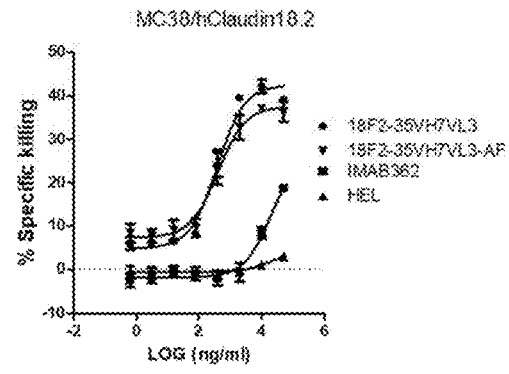
FIG. 22A        FIG. 22B

SEQUENCE LISTING

```
<160> NUMBER OF SEQ ID NOS: 90

<210> SEQ ID NO 1
<211> LENGTH: 5
<212> TYPE: PRT
<213> ORGANISM: Artificial Sequence
<220> FEATURE:
<223> OTHER INFORMATION: HV-CDR1

<400> SEQUENCE: 1

Ser Phe Trp Val Asn
1               5

<210> SEQ ID NO 2
<211> LENGTH: 5
<212> TYPE: PRT
<213> ORGANISM: Artificial Sequence
<220> FEATURE:
<223> OTHER INFORMATION: HV-CDR1

<400> SEQUENCE: 2

Ser Phe Trp Leu Asn
1               5

<210> SEQ ID NO 3
<211> LENGTH: 5
<212> TYPE: PRT
<213> ORGANISM: Artificial Sequence
<220> FEATURE:
<223> OTHER INFORMATION: HV-CDR3

<400> SEQUENCE: 3

Ser Phe Trp Ile Asn
1               5

<210> SEQ ID NO 4
<211> LENGTH: 17
<212> TYPE: PRT
<213> ORGANISM: Artificial Sequence
<220> FEATURE:
<223> OTHER INFORMATION: HV-CDR2

<400> SEQUENCE: 4

Asn Ile Tyr Pro Ser Thr Ser Tyr Thr Val Tyr Asn Gln Lys Phe Lys
1               5                   10                  15

Asp
```

```
<210> SEQ ID NO 5
<211> LENGTH: 17
<212> TYPE: PRT
<213> ORGANISM: Artificial Sequence
<220> FEATURE:
<223> OTHER INFORMATION: HV-CDR2

<400> SEQUENCE: 5

Asn Ile Tyr Pro Ser Thr Ser Tyr Thr Ile Tyr Asn Gln Lys Phe Lys
1               5                   10                  15

Asp

<210> SEQ ID NO 6
<211> LENGTH: 17
<212> TYPE: PRT
<213> ORGANISM: Artificial Sequence
<220> FEATURE:
<223> OTHER INFORMATION: HV-CDR2

<400> SEQUENCE: 6

Asn Ile Tyr Pro Ser Ala Ser Tyr Thr Val Tyr Asn Gln Lys Phe Lys
1               5                   10                  15

Asp

<210> SEQ ID NO 7
<211> LENGTH: 9
<212> TYPE: PRT
<213> ORGANISM: Artificial Sequence
<220> FEATURE:
<223> OTHER INFORMATION: HV-CDR3

<400> SEQUENCE: 7

Ser Trp Arg Gly Asn Ser Phe Asp His
1               5

<210> SEQ ID NO 8
<211> LENGTH: 9
<212> TYPE: PRT
<213> ORGANISM: Artificial Sequence
<220> FEATURE:
<223> OTHER INFORMATION: HV-CDR3

<400> SEQUENCE: 8

Thr Trp Arg Gly Asn Ser Phe Asp Leu
1               5

<210> SEQ ID NO 9
<211> LENGTH: 9
<212> TYPE: PRT
<213> ORGANISM: Artificial Sequence
<220> FEATURE:
<223> OTHER INFORMATION: HV-CDR3

<400> SEQUENCE: 9

Thr Trp Arg Gly Asn Ser Phe Asp Tyr
1               5

<210> SEQ ID NO 10
<211> LENGTH: 17
<212> TYPE: PRT
<213> ORGANISM: Artificial Sequence
<220> FEATURE:
<223> OTHER INFORMATION: LV-CDR1

<400> SEQUENCE: 10
```

```
-continued

Lys Ser Ser Gln Ser Leu Leu Asn Ser Gly Asn Gln Lys Asn Tyr Val
1               5                   10                  15

Thr

<210> SEQ ID NO 11
<211> LENGTH: 17
<212> TYPE: PRT
<213> ORGANISM: Artificial Sequence
<220> FEATURE:
<223> OTHER INFORMATION: LV-CDR2

<400> SEQUENCE: 11

Lys Ser Asn Gln Ser Leu Leu Asn Ser Gly Asn Gln Lys Asn Tyr Val
1               5                   10                  15

Thr

<210> SEQ ID NO 12
<211> LENGTH: 17
<212> TYPE: PRT
<213> ORGANISM: Artificial Sequence
<220> FEATURE:
<223> OTHER INFORMATION: LV-CDR1

<400> SEQUENCE: 12

Lys Ser Ser Gln Ser Leu Leu Asn Ser Gly Asn Gln Lys Asn Tyr Leu
1               5                   10                  15

Thr

<210> SEQ ID NO 13
<211> LENGTH: 7
<212> TYPE: PRT
<213> ORGANISM: Artificial Sequence
<220> FEATURE:
<223> OTHER INFORMATION: LV-CDR2

<400> SEQUENCE: 13

Trp Gly Ser Thr Arg Val Arg
1               5

<210> SEQ ID NO 14
<211> LENGTH: 7
<212> TYPE: PRT
<213> ORGANISM: Artificial Sequence
<220> FEATURE:
<223> OTHER INFORMATION: LV-CDR2

<400> SEQUENCE: 14

Trp Gly Ser Thr Arg Ser Thr
1               5

<210> SEQ ID NO 15
<211> LENGTH: 7
<212> TYPE: PRT
<213> ORGANISM: Artificial Sequence
<220> FEATURE:
<223> OTHER INFORMATION: LV-CDR2

<400> SEQUENCE: 15

Trp Ser Ser Thr Arg Ser Phe
1               5

<210> SEQ ID NO 16
<211> LENGTH: 9
<212> TYPE: PRT
<213> ORGANISM: Artificial Sequence
```

<220> FEATURE:
<223> OTHER INFORMATION: LV-CDR3

<400> SEQUENCE: 16

Gln Asn Asp Tyr Thr Tyr Pro Phe Thr
1               5

<210> SEQ ID NO 17
<211> LENGTH: 118
<212> TYPE: PRT
<213> ORGANISM: Artificial Sequence
<220> FEATURE:
<223> OTHER INFORMATION: HV

<400> SEQUENCE: 17

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Phe
            20                  25                  30

Trp Val Asn Trp Val Lys Gln Arg Pro Gly Gln Gly Leu Glu Trp Ile
        35                  40                  45

Gly Asn Ile Tyr Pro Ser Thr Ser Tyr Thr Val Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp His Trp Gly Gln Gly Thr
            100                 105                 110

Thr Leu Thr Val Ser Ser
        115

<210> SEQ ID NO 18
<211> LENGTH: 118
<212> TYPE: PRT
<213> ORGANISM: Artificial Sequence
<220> FEATURE:
<223> OTHER INFORMATION: HV

<400> SEQUENCE: 18

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Phe
            20                  25                  30

Trp Leu Asn Trp Val Lys Gln Arg Pro Gly Gln Gly Leu Glu Trp Ile
        35                  40                  45

Gly Asn Ile Tyr Pro Ser Thr Ser Tyr Thr Val Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Thr Trp Arg Gly Asn Ser Phe Asp Leu Trp Gly Gln Gly Thr
            100                 105                 110

Thr Leu Thr Val Ser Ser
        115

<210> SEQ ID NO 19
<211> LENGTH: 118

```
<212> TYPE: PRT
<213> ORGANISM: Artificial Sequence
<220> FEATURE:
<223> OTHER INFORMATION: HV

<400> SEQUENCE: 19

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Phe
            20                  25                  30

Trp Leu Asn Trp Val Lys Gln Arg Pro Gly Gln Gly Leu Glu Trp Ile
        35                  40                  45

Gly Asn Ile Tyr Pro Ser Thr Ser Tyr Thr Val Tyr Asn Gln Lys Phe
50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
            85                  90                  95

Thr Arg Thr Trp Arg Gly Asn Ser Phe Asp Tyr Trp Gly Gln Gly Thr
        100                 105                 110

Thr Leu Thr Val Ser Ser
        115

<210> SEQ ID NO 20
<211> LENGTH: 118
<212> TYPE: PRT
<213> ORGANISM: Artificial Sequence
<220> FEATURE:
<223> OTHER INFORMATION: HV

<400> SEQUENCE: 20

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Phe
            20                  25                  30

Trp Leu Asn Trp Val Lys Gln Arg Pro Gly Gln Gly Leu Glu Trp Ile
        35                  40                  45

Gly Asn Ile Tyr Pro Ser Thr Ser Tyr Thr Ile Tyr Asn Gln Lys Phe
50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
            85                  90                  95

Thr Arg Thr Trp Arg Gly Asn Ser Phe Asp Tyr Trp Gly Gln Gly Thr
        100                 105                 110

Thr Leu Thr Val Ser Ser
        115

<210> SEQ ID NO 21
<211> LENGTH: 118
<212> TYPE: PRT
<213> ORGANISM: Artificial Sequence
<220> FEATURE:
<223> OTHER INFORMATION: HV

<400> SEQUENCE: 21

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Phe
```

```
            20                  25                  30
Trp Ile Asn Trp Val Lys Gln Arg Pro Gly Gln Gly Leu Glu Trp Ile
            35                  40                  45
Gly Asn Ile Tyr Pro Ser Ala Ser Tyr Thr Val Tyr Asn Gln Lys Phe
        50                  55                  60
Lys Asp Lys Ala Thr Leu Thr Val Asp Lys Ser Ser Ser Thr Ala Tyr
65                  70                  75                  80
Met Gln Leu Ser Ser Pro Thr Ser Glu Asp Ser Ala Val Tyr Tyr Cys
                85                  90                  95
Thr Arg Thr Trp Arg Gly Asn Ser Phe Asp Leu Trp Gly Gln Gly Thr
            100                 105                 110
Thr Leu Thr Val Ser Ser
        115

<210> SEQ ID NO 22
<211> LENGTH: 118
<212> TYPE: PRT
<213> ORGANISM: Artificial Sequence
<220> FEATURE:
<223> OTHER INFORMATION: HV

<400> SEQUENCE: 22

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Phe
            20                  25                  30
Trp Leu Asn Trp Val Arg Gln Ala Pro Gly Gln Gly Leu Glu Trp Met
            35                  40                  45
Gly Asn Ile Tyr Pro Ser Thr Ser Tyr Thr Val Tyr Asn Gln Lys Phe
        50                  55                  60
Lys Asp Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Thr Trp Arg Gly Asn Ser Phe Asp Leu Trp Gly Gln Gly Thr
            100                 105                 110
Thr Val Thr Val Ser Ser
        115

<210> SEQ ID NO 23
<211> LENGTH: 118
<212> TYPE: PRT
<213> ORGANISM: Artificial Sequence
<220> FEATURE:
<223> OTHER INFORMATION: HV

<400> SEQUENCE: 23

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Phe
            20                  25                  30
Trp Leu Asn Trp Val Arg Gln Ala Pro Gly Gln Gly Leu Glu Trp Ile
            35                  40                  45
Gly Asn Ile Tyr Pro Ser Thr Ser Tyr Thr Val Tyr Asn Gln Lys Phe
        50                  55                  60
Lys Asp Arg Val Thr Leu Thr Val Asp Lys Ser Thr Ser Thr Val Tyr
65                  70                  75                  80
```

```
Met Glu Leu Ser Ser Leu Arg Ser Glu Asp Thr Ala Val Tyr Tyr Cys
                 85                  90                  95

Ala Arg Thr Trp Arg Gly Asn Ser Phe Asp Leu Trp Gly Gln Gly Thr
            100                 105                 110

Thr Val Thr Val Ser Ser
            115

<210> SEQ ID NO 24
<211> LENGTH: 118
<212> TYPE: PRT
<213> ORGANISM: Artificial Sequence
<220> FEATURE:
<223> OTHER INFORMATION: HV

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Leu Asn Trp Val Arg Gln Ala Pro Gly Gln Gly Leu Glu Trp Ile
            35                  40                  45

Gly Asn Ile Tyr Pro Ser Thr Ser Tyr Thr Val Tyr Asn Gln Lys Phe
        50                  55                  60

Lys Asp Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Trp Arg Gly Asn Ser Phe Asp Leu Trp Gly Gln Gly Thr
            100                 105                 110

Thr Val Thr Val Ser Ser
            115

<210> SEQ ID NO 25
<211> LENGTH: 118
<212> TYPE: PRT
<213> ORGANISM: Artificial Sequence
<220> FEATURE:
<223> OTHER INFORMATION: HV

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Leu Asn Trp Val Arg Gln Arg Pro Gly Gln Gly Leu Glu Trp Ile
            35                  40                  45

Gly Asn Ile Tyr Pro Ser Thr Ser Tyr Thr Val Tyr Asn Gln Lys Phe
        50                  55                  60

Lys Asp Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Trp Arg Gly Asn Ser Phe Asp Leu Trp Gly Gln Gly Thr
            100                 105                 110

Thr Val Thr Val Ser Ser
            115

<210> SEQ ID NO 26
```

-continued

<211> LENGTH: 118
<212> TYPE: PRT
<213> ORGANISM: Artificial Sequence
<220> FEATURE:
<223> OTHER INFORMATION: HV

<400> SEQUENCE: 26

```
Gln Val Gln Leu Val Gln Ser Gly Ala Glu Val Lys Lys Pro Gly Ala
1               5                  10                  15
Ser Val Lys Val Ser Cys Lys Ala Ser Gly Tyr Thr Phe Thr Ser Phe
            20                  25                  30
Trp Leu Asn Trp Val Arg Gln Arg Pro Gly Gln Gly Leu Glu Trp Ile
        35                  40                  45
Gly Asn Ile Tyr Pro Ser Thr Ser Tyr Thr Val Tyr Asn Gln Lys Phe
    50                  55                  60
Lys Asp Arg Val Thr Leu Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Thr Arg Thr Trp Arg Gly Asn Ser Phe Asp Leu Trp Gly Gln Gly Thr
            100                 105                 110
Thr Val Thr Val Ser Ser
        115
```

<210> SEQ ID NO 27
<211> LENGTH: 118
<212> TYPE: PRT
<213> ORGANISM: Artificial Sequence
<220> FEATURE:
<223> OTHER INFORMATION: HV

<400> SEQUENCE: 27

```
Gln Val Gln Leu Val Gln Ser Gly Ala Glu Val Lys Lys Pro Gly Ala
1               5                  10                  15
Ser Val Lys Val Ser Cys Lys Ala Ser Gly Tyr Thr Phe Thr Ser Phe
            20                  25                  30
Trp Leu Asn Trp Val Arg Gln Arg Pro Gly Gln Gly Leu Glu Trp Ile
        35                  40                  45
Gly Asn Ile Tyr Pro Ser Thr Ser Tyr Thr Val Tyr Asn Gln Lys Phe
    50                  55                  60
Lys Asp Arg Val Thr Leu Thr Val Asp Lys Ser Ser Ser Thr Ala Tyr
65                  70                  75                  80
Met Glu Leu Ser Ser Leu Thr Ser Glu Asp Thr Ala Val Tyr Tyr Cys
                85                  90                  95
Thr Arg Thr Trp Arg Gly Asn Ser Phe Asp Leu Trp Gly Gln Gly Thr
            100                 105                 110
Thr Val Thr Val Ser Ser
        115
```

<210> SEQ ID NO 28
<211> LENGTH: 118
<212> TYPE: PRT
<213> ORGANISM: Artificial Sequence
<220> FEATURE:
<223> OTHER INFORMATION: HV

<400> SEQUENCE: 28

```
Gln Val Gln Leu Val Gln Ser Gly Ala Glu Val Lys Lys Pro Gly Ala
1               5                  10                  15
```

```
Ser Val Lys Val Ser Cys Lys Ala Ser Gly Tyr Thr Phe Thr Ser Phe
            20                  25                  30

Trp Leu Asn Trp Val Lys Gln Arg Pro Gly Gln Gly Leu Glu Trp Ile
        35                  40                  45

Gly Asn Ile Tyr Pro Ser Thr Ser Tyr Thr Val Tyr Asn Gln Lys Phe
    50                  55                  60

Lys Asp Lys Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Thr Arg Thr Trp Arg Gly Asn Ser Phe Asp Leu Trp Gly Gln Gly Thr
            100                 105                 110

Thr Val Thr Val Ser Ser
        115

<210> SEQ ID NO 29
<211> LENGTH: 118
<212> TYPE: PRT
<213> ORGANISM: Artificial Sequence
<220> FEATURE:
<223> OTHER INFORMATION: HV

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Leu Asn Trp Val Arg Gln Ala Pro Gly Gln Gly Leu Glu Trp Met
        35                  40                  45

Gly Asn Ile Tyr Pro Ser Thr Ser Tyr Thr Val Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Thr Trp Arg Gly Asn Ser Phe Asp Tyr Trp Gly Gln Gly Thr
            100                 105                 110

Thr Val Thr Val Ser Ser
        115

<210> SEQ ID NO 30
<211> LENGTH: 118
<212> TYPE: PRT
<213> ORGANISM: Artificial Sequence
<220> FEATURE:
<223> OTHER INFORMATION: HV

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Leu Asn Trp Val Arg Gln Ala Pro Gly Gln Gly Leu Glu Trp Ile
        35                  40                  45

Gly Asn Ile Tyr Pro Ser Thr Ser Tyr Thr Val Tyr Asn Gln Lys Phe
    50                  55                  60

Lys Asp Arg Val Thr Leu Thr Val Asp Lys Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Thr Trp Arg Gly Asn Ser Phe Asp Tyr Trp Gly Gln Gly Thr
            100                 105                 110

Thr Val Thr Val Ser Ser
        115

<210> SEQ ID NO 31
<211> LENGTH: 118
<212> TYPE: PRT
<213> ORGANISM: Artificial Sequence
<220> FEATURE:
<223> OTHER INFORMATION: HV

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Leu Asn Trp Val Arg Gln Ala Pro Gly Gln Gly Leu Glu Trp Ile
        35                  40                  45

Gly Asn Ile Tyr Pro Ser Thr Ser Tyr Thr Val Tyr Asn Gln Lys Phe
    50                  55                  60

Lys Asp Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Trp Arg Gly Asn Ser Phe Asp Tyr Trp Gly Gln Gly Thr
            100                 105                 110

Thr Val Thr Val Ser Ser
        115

<210> SEQ ID NO 32
<211> LENGTH: 118
<212> TYPE: PRT
<213> ORGANISM: Artificial Sequence
<220> FEATURE:
<223> OTHER INFORMATION: HV

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Leu Asn Trp Val Arg Gln Arg Pro Gly Gln Gly Leu Glu Trp Ile
        35                  40                  45

Gly Asn Ile Tyr Pro Ser Thr Ser Tyr Thr Val Tyr Asn Gln Lys Phe
    50                  55                  60

Lys Asp Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Trp Arg Gly Asn Ser Phe Asp Tyr Trp Gly Gln Gly Thr
            100                 105                 110

Thr Val Thr Val Ser Ser
        115
```

```
<210> SEQ ID NO 33
<211> LENGTH: 118
<212> TYPE: PRT
<213> ORGANISM: Artificial Sequence
<220> FEATURE:
<223> OTHER INFORMATION: HV

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Leu Asn Trp Val Arg Gln Arg Pro Gly Gln Gly Leu Glu Trp Ile
        35                  40                  45

Gly Asn Ile Tyr Pro Ser Thr Ser Tyr Thr Val Tyr Asn Gln Lys Phe
    50                  55                  60

Lys Asp Arg Val Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Trp Arg Gly Asn Ser Phe Asp Tyr Trp Gly Gln Gly Thr
            100                 105                 110

Thr Val Thr Val Ser Ser
        115

<210> SEQ ID NO 34
<211> LENGTH: 118
<212> TYPE: PRT
<213> ORGANISM: Artificial Sequence
<220> FEATURE:
<223> OTHER INFORMATION: HV

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Leu Asn Trp Val Arg Gln Arg Pro Gly Gln Gly Leu Glu Trp Ile
        35                  40                  45

Gly Asn Ile Tyr Pro Ser Thr Ser Tyr Thr Val Tyr Asn Gln Lys Phe
    50                  55                  60

Lys Asp Arg Val Thr Leu Thr Val Asp Lys Ser Ser Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Thr Trp Arg Gly Asn Ser Phe Asp Tyr Trp Gly Gln Gly Thr
            100                 105                 110

Thr Val Thr Val Ser Ser
        115

<210> SEQ ID NO 35
<211> LENGTH: 118
<212> TYPE: PRT
<213> ORGANISM: Artificial Sequence
<220> FEATURE:
<223> OTHER INFORMATION: HV

<400> SEQUENCE: 35

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Phe
            20                  25                  30

Trp Leu Asn Trp Val Lys Gln Arg Pro Gly Gln Gly Leu Glu Trp Ile
        35                  40                  45

Gly Asn Ile Tyr Pro Ser Thr Ser Tyr Thr Val Tyr Asn Gln Lys Phe
    50                  55                  60

Lys Asp Lys Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Thr Arg Thr Trp Arg Gly Asn Ser Phe Asp Tyr Trp Gly Gln Gly Thr
            100                 105                 110

Thr Val Thr Val Ser Ser
            115

<210> SEQ ID NO 36
<211> LENGTH: 118
<212> TYPE: PRT
<213> ORGANISM: Artificial Sequence
<220> FEATURE:
<223> OTHER INFORMATION: HV

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Leu Asn Trp Val Arg Gln Ala Pro Gly Gln Gly Leu Glu Trp Met
        35                  40                  45

Gly Asn Ile Tyr Pro Ser Ser Tyr Thr Ile Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Thr Trp Arg Gly Asn Ser Phe Asp Tyr Trp Gly Gln Gly Thr
            100                 105                 110

Thr Val Thr Val Ser Ser
            115

<210> SEQ ID NO 37
<211> LENGTH: 118
<212> TYPE: PRT
<213> ORGANISM: Artificial Sequence
<220> FEATURE:
<223> OTHER INFORMATION: HV

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Leu Asn Trp Val Arg Gln Ala Pro Gly Gln Gly Leu Glu Trp Ile
        35                  40                  45

Gly Asn Ile Tyr Pro Ser Thr Ser Tyr Thr Ile Tyr Asn Gln Lys Phe
    50                  55                  60

Lys Asp Arg Val Thr Leu Thr Val Asp Lys Ser Thr Ser Thr Val Tyr
```

```
                65                  70                  75                  80
Met Glu Leu Ser Ser Leu Arg Ser Glu Asp Thr Ala Val Tyr Tyr Cys
                    85                  90                  95

Ala Arg Thr Trp Arg Gly Asn Ser Phe Asp Tyr Trp Gly Gln Gly Thr
                100                 105                 110

Thr Val Thr Val Ser Ser
        115

<210> SEQ ID NO 38
<211> LENGTH: 118
<212> TYPE: PRT
<213> ORGANISM: Artificial Sequence
<220> FEATURE:
<223> OTHER INFORMATION: HV

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
                20                  25                  30

Trp Leu Asn Trp Val Arg Gln Ala Pro Gly Gln Gly Leu Glu Trp Ile
            35                  40                  45

Gly Asn Ile Tyr Pro Ser Thr Ser Tyr Thr Ile Tyr Asn Gln Lys Phe
        50                  55                  60

Lys Asp Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Ala Arg Thr Trp Arg Gly Asn Ser Phe Asp Tyr Trp Gly Gln Gly Thr
                100                 105                 110

Thr Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: HV

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
                20                  25                  30

Trp Leu Asn Trp Val Arg Gln Arg Pro Gly Gln Gly Leu Glu Trp Ile
            35                  40                  45

Gly Asn Ile Tyr Pro Ser Thr Ser Tyr Thr Ile Tyr Asn Gln Lys Phe
        50                  55                  60

Lys Asp Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Ala Arg Thr Trp Arg Gly Asn Ser Phe Asp Tyr Trp Gly Gln Gly Thr
                100                 105                 110

Thr Val Thr Val Ser Ser
        115
```

```
<210> SEQ ID NO 40
<211> LENGTH: 118
<212> TYPE: PRT
<213> ORGANISM: Artificial Sequence
<220> FEATURE:
<223> OTHER INFORMATION: HV

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
                20                  25                  30

Trp Leu Asn Trp Val Arg Gln Arg Pro Gly Gln Gly Leu Glu Trp Ile
            35                  40                  45

Gly Asn Ile Tyr Pro Ser Thr Ser Tyr Thr Ile Tyr Asn Gln Lys Phe
    50                  55                  60

Lys Asp Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Trp Arg Gly Asn Ser Phe Asp Tyr Trp Gly Gln Gly Thr
            100                 105                 110

Thr Val Thr Val Ser Ser
        115

<210> SEQ ID NO 41
<211> LENGTH: 118
<212> TYPE: PRT
<213> ORGANISM: Artificial Sequence
<220> FEATURE:
<223> OTHER INFORMATION: HV

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
                20                  25                  30

Trp Leu Asn Trp Val Arg Gln Arg Pro Gly Gln Gly Leu Glu Trp Ile
            35                  40                  45

Gly Asn Ile Tyr Pro Ser Thr Ser Tyr Thr Ile Tyr Asn Gln Lys Phe
    50                  55                  60

Lys Asp Arg Val Thr Leu Thr Val Asp Lys Ser Ser Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Thr Trp Arg Gly Asn Ser Phe Asp Tyr Trp Gly Gln Gly Thr
            100                 105                 110

Thr Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: HV

<400> SEQUENCE: 42

Gln Val Gln Leu Val Gln Ser Gly Ala Glu Val Lys Lys Pro Gly Ala
```

-continued

```
                1               5                      10                     15
Ser Val Lys Val Ser Cys Lys Ala Ser Gly Tyr Thr Phe Thr Ser Phe
                20                      25                     30

Trp Leu Asn Trp Val Lys Gln Arg Pro Gly Gln Gly Leu Glu Trp Ile
                35                      40                     45

Gly Asn Ile Tyr Pro Ser Thr Ser Tyr Thr Ile Tyr Asn Gln Lys Phe
                50                      55                     60

Lys Asp Lys Val Thr Leu Thr Val Asp Lys Ser Thr Ser Thr Ala Tyr
65                      70                     75                     80

Met Glu Leu Ser Ser Leu Arg Ser Glu Asp Thr Ala Val Tyr Tyr Cys
                85                      90                     95

Thr Arg Thr Trp Arg Gly Asn Ser Phe Asp Tyr Trp Gly Gln Gly Thr
                100                     105                    110

Thr Val Thr Val Ser Ser
                115
```

<210> SEQ ID NO 43
<211> LENGTH: 118
<212> TYPE: PRT
<213> ORGANISM: Artificial Sequence
<220> FEATURE:
<223> OTHER INFORMATION: HV

<400> SEQUENCE: 43

```
Gln Val Gln Leu Val Gln Ser Gly Ala Glu Val Lys Lys Pro Gly Ala
1               5                      10                     15

Ser Val Lys Val Ser Cys Lys Ala Ser Gly Tyr Thr Phe Thr Ser Phe
                20                      25                     30

Trp Ile Asn Trp Val Arg Gln Ala Pro Gly Gln Gly Leu Glu Trp Met
                35                      40                     45

Gly Asn Ile Tyr Pro Ser Ala Ser Tyr Thr Val Tyr Asn Gln Lys Phe
                50                      55                     60

Lys Asp Arg Val Thr Met Thr Arg Asp Thr Ser Thr Ser Thr Val Tyr
65                      70                     75                     80

Met Glu Leu Ser Ser Leu Arg Ser Glu Asp Thr Ala Val Tyr Tyr Cys
                85                      90                     95

Ala Arg Thr Trp Arg Gly Asn Ser Phe Asp Leu Trp Gly Gln Gly Thr
                100                     105                    110

Thr Val Thr Val Ser Ser
                115
```

<210> SEQ ID NO 44
<211> LENGTH: 118
<212> TYPE: PRT
<213> ORGANISM: Artificial Sequence
<220> FEATURE:
<223> OTHER INFORMATION: HV

<400> SEQUENCE: 44

```
Gln Val Gln Leu Val Gln Ser Gly Ala Glu Val Lys Lys Pro Gly Ala
1               5                      10                     15

Ser Val Lys Val Ser Cys Lys Ala Ser Gly Tyr Thr Phe Thr Ser Phe
                20                      25                     30

Trp Ile Asn Trp Val Arg Gln Ala Pro Gly Gln Gly Leu Glu Trp Ile
                35                      40                     45

Gly Asn Ile Tyr Pro Ser Ala Ser Tyr Thr Val Tyr Asn Gln Lys Phe
                50                      55                     60
```

```
Lys Asp Arg Val Thr Leu Thr Val Asp Lys Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Thr Trp Arg Gly Asn Ser Phe Asp Leu Trp Gly Gln Gly Thr
                100                 105                 110

Thr Val Thr Val Ser Ser
            115

<210> SEQ ID NO 45
<211> LENGTH: 118
<212> TYPE: PRT
<213> ORGANISM: Artificial Sequence
<220> FEATURE:
<223> OTHER INFORMATION: HV

<400> SEQUENCE: 45

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Phe
                20                  25                  30

Trp Ile Asn Trp Val Arg Gln Ala Pro Gly Gln Gly Leu Glu Trp Ile
             35                  40                  45

Gly Asn Ile Tyr Pro Ser Ala Ser Tyr Thr Val Tyr Asn Gln Lys Phe
 50                  55                  60

Lys Asp Arg Val Thr Leu Thr Val Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Thr Trp Arg Gly Asn Ser Phe Asp Leu Trp Gly Gln Gly Thr
                100                 105                 110

Thr Val Thr Val Ser Ser
            115

<210> SEQ ID NO 46
<211> LENGTH: 118
<212> TYPE: PRT
<213> ORGANISM: Artificial Sequence
<220> FEATURE:
<223> OTHER INFORMATION: HV

<400> SEQUENCE: 46

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Phe
                20                  25                  30

Trp Ile Asn Trp Val Arg Gln Arg Pro Gly Gln Gly Leu Glu Trp Ile
             35                  40                  45

Gly Asn Ile Tyr Pro Ser Ala Ser Tyr Thr Val Tyr Asn Gln Lys Phe
 50                  55                  60

Lys Asp Arg Val Thr Leu Thr Val Asp Lys Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Thr Trp Arg Gly Asn Ser Phe Asp Leu Trp Gly Gln Gly Thr
                100                 105                 110

Thr Val Thr Val Ser Ser
            115
```

<210> SEQ ID NO 47
<211> LENGTH: 118
<212> TYPE: PRT
<213> ORGANISM: Artificial Sequence
<220> FEATURE:
<223> OTHER INFORMATION: HV

<400> SEQUENCE: 47

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Ile Asn Trp Val Arg Gln Arg Pro Gly Gln Gly Leu Glu Trp Ile
        35                  40                  45

Gly Asn Ile Tyr Pro Ser Ala Ser Tyr Thr Val Tyr Asn Gln Lys Phe
    50                  55                  60

Lys Asp Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Trp Arg Gly Asn Ser Phe Asp Leu Trp Gly Gln Gly Thr
            100                 105                 110

Thr Val Thr Val Ser Ser
        115
```

<210> SEQ ID NO 48
<211> LENGTH: 118
<212> TYPE: PRT
<213> ORGANISM: Artificial Sequence
<220> FEATURE:
<223> OTHER INFORMATION: HV

<400> SEQUENCE: 48

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Ile Asn Trp Val Arg Gln Arg Pro Gly Gln Gly Leu Glu Trp Ile
        35                  40                  45

Gly Asn Ile Tyr Pro Ser Ala Ser Tyr Thr Val Tyr Asn Gln Lys Phe
    50                  55                  60

Lys Asp Arg Val Thr Leu Thr Val Asp Lys Ser Ser Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Thr Trp Arg Gly Asn Ser Phe Asp Leu Trp Gly Gln Gly Thr
            100                 105                 110

Thr Val Thr Val Ser Ser
        115
```

<210> SEQ ID NO 49
<211> LENGTH: 118
<212> TYPE: PRT
<213> ORGANISM: Artificial Sequence
<220> FEATURE:
<223> OTHER INFORMATION: HV

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Ile Asn Trp Val Lys Gln Arg Pro Gly Gln Gly Leu Glu Trp Ile
        35                  40                  45

Gly Asn Ile Tyr Pro Ser Ala Ser Tyr Thr Val Tyr Asn Gln Lys Phe
    50                  55                  60

Lys Asp Lys Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Trp Arg Gly Asn Ser Phe Asp Leu Trp Gly Gln Gly Thr
                100                 105                 110

Thr Val Thr Val Ser Ser
            115

<210> SEQ ID NO 50
<211> LENGTH: 113
<212> TYPE: PRT
<213> ORGANISM: Artificial Sequence
<220> FEATURE:
<223> OTHER INFORMATION: LV

<400> SEQUENCE: 50

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Val Thr Trp Tyr Gln Gln Lys Pro Gly Gln
        35                  40                  45

Pro Pro Lys Leu Leu Ile Tyr Trp Gly Ser Thr Arg Val Arg Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Thr Tyr Pro Phe Thr Phe Gly Ser Gly Thr Lys Leu Glu Ile
                100                 105                 110

Lys

<210> SEQ ID NO 51
<211> LENGTH: 113
<212> TYPE: PRT
<213> ORGANISM: Artificial Sequence
<220> FEATURE:
<223> OTHER INFORMATION: LV

<400> SEQUENCE: 51

Asp Ile Val Met Thr Gln Ser Pro Ser Ser Leu Thr Val Thr Ala Gly
1               5                   10                  15

Glu Lys Val Thr Met Ser Cys Lys Ser Asn Gln Ser Leu Leu Asn Ser
            20                  25                  30

Gly Asn Gln Lys Asn Tyr Val Thr Trp Tyr Gln Gln Lys Pro Gly Gln
        35                  40                  45

Pro Pro Lys Leu Leu Ile Tyr Trp Gly Ser Thr Arg Val Arg Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Thr Tyr Pro Phe Thr Phe Gly Ser Gly Thr Lys Leu Glu Ile
                100                 105                 110

Lys

<210> SEQ ID NO 52
<211> LENGTH: 113
<212> TYPE: PRT
<213> ORGANISM: Artificial Sequence
<220> FEATURE:
<223> OTHER INFORMATION: LV

<400> SEQUENCE: 52

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Val Thr Trp Tyr Gln Gln Lys Pro Gly Gln
            35                  40                  45

Pro Pro Lys Leu Leu Ile Tyr Trp Gly Ser Thr Arg Ser Thr Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Thr Tyr Pro Phe Thr Phe Gly Ser Gly Thr Lys Leu Glu Ile
                100                 105                 110

Lys

<210> SEQ ID NO 53
<211> LENGTH: 113
<212> TYPE: PRT
<213> ORGANISM: Artificial Sequence
<220> FEATURE:
<223> OTHER INFORMATION: LV

<400> SEQUENCE: 53

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Gly Ser Thr Arg Val Arg Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Thr Tyr Pro Phe Thr Phe Gly Ser Gly Thr Lys Leu Glu Ile
                100                 105                 110

Lys

<210> SEQ ID NO 54

<211> LENGTH: 113
<212> TYPE: PRT
<213> ORGANISM: Artificial Sequence
<220> FEATURE:
<223> OTHER INFORMATION: LV

<400> SEQUENCE: 54

Asp Ile Val Met Thr Gln Ser Pro Ser Ser Leu Thr Val Thr Ala Gly
1               5                   10                  15
Glu Lys Val Thr Met Ser Cys Lys Ser Gln Ser Leu Leu Asn Ser
            20                  25                  30
Gly Asn Gln Lys Asn Tyr Val Thr Trp Tyr Gln Gln Lys Pro Gly Gln
        35                  40                  45
Pro Pro Lys Leu Leu Ile Tyr Trp Ser Ser Thr Arg Ser Phe Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Gln Asn
                85                  90                  95
Asp Tyr Thr Tyr Pro Phe Thr Phe Gly Ser Gly Thr Lys Leu Glu Ile
            100                 105                 110
Lys

<210> SEQ ID NO 55
<211> LENGTH: 113
<212> TYPE: PRT
<213> ORGANISM: Artificial Sequence
<220> FEATURE:
<223> OTHER INFORMATION: LV

<400> SEQUENCE: 55

Asp Ile Val Met Thr Gln Ser Pro Asp Ser Leu Ala Val Ser Leu Gly
1               5                   10                  15
Glu Arg Ala Thr Ile Asn Cys Lys Ser Asn Gln Ser Leu Leu Asn Ser
            20                  25                  30
Gly Asn Gln Lys Asn Tyr Val Thr Trp Tyr Gln Gln Lys Pro Gly Gln
        35                  40                  45
Pro Pro Lys Leu Leu Ile Tyr Trp Gly Ser Thr Arg Val Arg Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Asn
                85                  90                  95
Asp Tyr Thr Tyr Pro Phe Thr Phe Gly Gln Gly Thr Lys Leu Glu Ile
            100                 105                 110
Lys

<210> SEQ ID NO 56
<211> LENGTH: 113
<212> TYPE: PRT
<213> ORGANISM: Artificial Sequence
<220> FEATURE:
<223> OTHER INFORMATION: LV

<400> SEQUENCE: 56

Asp Ile Val Met Thr Gln Ser Pro Ser Ser Leu Thr Val Ser Leu Gly
1               5                   10                  15
Glu Lys Ala Thr Ile Asn Cys Lys Ser Asn Gln Ser Leu Leu Asn Ser
            20                  25                  30

```
Gly Asn Gln Lys Asn Tyr Val Thr Trp Tyr Gln Gln Lys Pro Gly Gln
            35                  40                  45

Pro Pro Lys Leu Leu Ile Tyr Trp Gly Ser Thr Arg Val Arg Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Leu Ala Val Tyr Tyr Cys Gln Asn
                 85                  90                  95

Asp Tyr Thr Tyr Pro Phe Thr Phe Gly Gln Gly Thr Lys Leu Glu Ile
            100                 105                 110

Lys

<210> SEQ ID NO 57
<211> LENGTH: 113
<212> TYPE: PRT
<213> ORGANISM: Artificial Sequence
<220> FEATURE:
<223> OTHER INFORMATION: LV

<400> SEQUENCE: 57

Asp Ile Val Met Thr Gln Ser Pro Ser Ser Leu Thr Val Ser Leu Gly
 1               5                  10                  15

Glu Lys Ala Thr Ile Ser Cys Lys Ser Asn Gln Ser Leu Leu Asn Ser
            20                  25                  30

Gly Asn Gln Lys Asn Tyr Val Thr Trp Tyr Gln Gln Lys Pro Gly Gln
            35                  40                  45

Pro Pro Lys Leu Leu Ile Tyr Trp Gly Ser Thr Arg Val Arg Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Leu Ala Val Tyr Tyr Cys Gln Asn
                 85                  90                  95

Asp Tyr Thr Tyr Pro Phe Thr Phe Gly Ser Gly Thr Lys Leu Glu Ile
            100                 105                 110

Lys

<210> SEQ ID NO 58
<211> LENGTH: 113
<212> TYPE: PRT
<213> ORGANISM: Artificial Sequence
<220> FEATURE:
<223> OTHER INFORMATION: LV

<400> SEQUENCE: 58

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
            20                  25                  30

Gly Asn Gln Lys Asn Tyr Val Thr Trp Tyr Gln Gln Lys Pro Gly Gln
            35                  40                  45

Pro Pro Lys Leu Leu Ile Tyr Trp Gly Ser Thr Arg Ser Thr Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95
```

Asp Tyr Thr Tyr Pro Phe Thr Phe Gly Gln Gly Thr Lys Leu Glu Ile
            100                 105                 110

Lys

<210> SEQ ID NO 59
<211> LENGTH: 113
<212> TYPE: PRT
<213> ORGANISM: Artificial Sequence
<220> FEATURE:
<223> OTHER INFORMATION: LV

<400> SEQUENCE: 59

Asp Ile Val Met Thr Gln Ser Pro Ser Ser Leu Thr Val Ser Leu Gly
1               5                   10                  15

Glu Lys Ala Thr Ile Asn Cys Lys Ser Gln Ser Leu Leu Asn Ser
            20                  25                  30

Gly Asn Gln Lys Asn Tyr Val Thr Trp Tyr Gln Gln Lys Pro Gly Gln
        35                  40                  45

Pro Pro Lys Leu Leu Ile Tyr Trp Gly Ser Thr Arg Ser Thr Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Leu Ala Val Tyr Tyr Cys Gln Asn
                85                  90                  95

Asp Tyr Thr Tyr Pro Phe Thr Phe Gly Gln Gly Thr Lys Leu Glu Ile
            100                 105                 110

Lys

<210> SEQ ID NO 60
<211> LENGTH: 113
<212> TYPE: PRT
<213> ORGANISM: Artificial Sequence
<220> FEATURE:
<223> OTHER INFORMATION: LV

<400> SEQUENCE: 60

Asp Ile Val Met Thr Gln Ser Pro Ser Ser Leu Thr Val Ser Leu Gly
1               5                   10                  15

Glu Lys Ala Thr Ile Ser Cys Lys Ser Gln Ser Leu Leu Asn Ser
            20                  25                  30

Gly Asn Gln Lys Asn Tyr Val Thr Trp Tyr Gln Gln Lys Pro Gly Gln
        35                  40                  45

Pro Pro Lys Leu Leu Ile Tyr Trp Gly Ser Thr Arg Ser Thr Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Leu Ala Val Tyr Tyr Cys Gln Asn
                85                  90                  95

Asp Tyr Thr Tyr Pro Phe Thr Phe Gly Ser Gly Thr Lys Leu Glu Ile
            100                 105                 110

Lys

<210> SEQ ID NO 61
<211> LENGTH: 113
<212> TYPE: PRT
<213> ORGANISM: Artificial Sequence
<220> FEATURE:
<223> OTHER INFORMATION: LV -continued

```
<400> SEQUENCE: 61

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Gly Ser Thr Arg Val Arg Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Phe Thr Phe Gly Gln Gly Thr Lys Leu Glu Ile
            100                 105                 110

Lys

<210> SEQ ID NO 62
<211> LENGTH: 113
<212> TYPE: PRT
<213> ORGANISM: Artificial Sequence
<220> FEATURE:
<223> OTHER INFORMATION: LV

<400> SEQUENCE: 62

Asp Ile Val Met Thr Gln Ser Pro Ser Ser Leu Thr Val Ser Leu Gly
1               5                   10                  15

Glu Lys Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Gly Ser Thr Arg Val Arg Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Leu Ala Val Tyr Tyr Cys Gln Asn
                85                  90                  95

Asp Tyr Thr Tyr Pro Phe Thr Phe Gly Gln Gly Thr Lys Leu Glu Ile
            100                 105                 110

Lys

<210> SEQ ID NO 63
<211> LENGTH: 113
<212> TYPE: PRT
<213> ORGANISM: Artificial Sequence
<220> FEATURE:
<223> OTHER INFORMATION: LV

<400> SEQUENCE: 63

Asp Ile Val Met Thr Gln Ser Pro Ser Ser Leu Thr Val Ser Leu Gly
1               5                   10                  15

Glu Lys Ala Thr Ile Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Gly Ser Thr Arg Val Arg Gly Val
50                  55                  60
```

```
Pro Asp Arg Phe Ser Gly Ser Gly Ser Gly Thr Asp Phe Thr Leu Thr
 65                  70                  75                  80

Ile Ser Ser Leu Gln Ala Glu Asp Leu Ala Val Tyr Tyr Cys Gln Asn
                 85                  90                  95

Asp Tyr Thr Tyr Pro Phe Thr Phe Gly Ser Gly Thr Lys Leu Glu Ile
            100                 105                 110

Lys

<210> SEQ ID NO 64
<211> LENGTH: 113
<212> TYPE: PRT
<213> ORGANISM: Artificial Sequence
<220> FEATURE:
<223> OTHER INFORMATION: LV

<400> SEQUENCE: 64

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Asn Ser
                 20                  25                  30

Gly Asn Gln Lys Asn Tyr Val Thr Trp Tyr Gln Gln Lys Pro Gly Gln
             35                  40                  45

Pro Pro Lys Leu Leu Ile Tyr Trp Ser Thr Arg Ser Phe Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Thr Tyr Pro Phe Thr Phe Gly Gln Gly Thr Lys Leu Glu Ile
            100                 105                 110

Lys

<210> SEQ ID NO 65
<211> LENGTH: 113
<212> TYPE: PRT
<213> ORGANISM: Artificial Sequence
<220> FEATURE:
<223> OTHER INFORMATION: LV

<400> SEQUENCE: 65

Asp Ile Val Met Thr Gln Ser Pro Ser Ser Leu Thr Val Ser Leu Gly
  1               5                  10                  15

Glu Lys Ala Thr Ile Asn Cys Lys Ser Ser Gln Ser Leu Leu Asn Ser
                 20                  25                  30

Gly Asn Gln Lys Asn Tyr Val Thr Trp Tyr Gln Gln Lys Pro Gly Gln
             35                  40                  45

Pro Pro Lys Leu Leu Ile Tyr Trp Ser Thr Arg Ser Phe Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Leu Ala Val Tyr Tyr Cys Gln Asn
                 85                  90                  95

Asp Tyr Thr Tyr Pro Phe Thr Phe Gly Gln Gly Thr Lys Leu Glu Ile
            100                 105                 110

Lys
```

```
<210> SEQ ID NO 66
<211> LENGTH: 113
<212> TYPE: PRT
<213> ORGANISM: Artificial Sequence
<220> FEATURE:
<223> OTHER INFORMATION: LV

<400> SEQUENCE: 66

Asp Ile Val Met Thr Gln Ser Pro Ser Ser Leu Thr Val Ser Leu Gly
1               5                   10                  15

Glu Lys Ala Thr Ile Ser Cys Lys Ser Gln Ser Leu Leu Asn Ser
            20                  25                  30

Gly Asn Gln Lys Asn Tyr Val Thr Trp Tyr Gln Gln Lys Pro Gly Gln
        35                  40                  45

Pro Pro Lys Leu Leu Ile Tyr Trp Ser Thr Arg Ser Phe Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Leu Ala Val Tyr Tyr Cys Gln Asn
                85                  90                  95

Asp Tyr Thr Tyr Pro Phe Thr Phe Gly Ser Gly Thr Lys Leu Glu Ile
            100                 105                 110

Lys

<210> SEQ ID NO 67
<211> LENGTH: 330
<212> TYPE: PRT
<213> ORGANISM: Artificial Sequence
<220> FEATURE:
<223> OTHER INFORMATION: HC

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
              195                 200                 205
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 68
<211> LENGTH: 107
<212> TYPE: PRT
<213> ORGANISM: Artificial Sequence
<220> FEATURE:
<223> OTHER INFORMATION: LC

<400> SEQUENCE: 68

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 69
<211> LENGTH: 786
<212> TYPE: DNA
<213> ORGANISM: Homo sapiens

<400> SEQUENCE: 69
atgagcacca ccacctgcca ggtggtggcc ttcctgctga gcatcctggg cctggccggc       60
tgcatcgccg ccaccggcat ggacatgtgg agcacccagg acctgtacga caaccccgtg      120
accagcgtgt tccagtacga gggcctgtgg cgcagctgcg tgcgccagag cagcggcttc      180
accgagtgcc gccctactt caccatcctg ggctgcccg ccatgctgca ggccgtgcgc      240
gccctgatga tcgtgggcat cgtgctgggc ccatcggcc tgctggtgag catcttcgcc      300
ctgaagtgca tccgcatcgg cagcatggag acagcgcca aggccaacat gacccctgacc      360 agcggcatca tgttcatcgt gagcggcctg tgcgccatcg ccggcgtgag cgtgttcgcc      420
```

```
aacatgctgg tgaccaactt ctggatgagc accgccaaca tgtacaccgg catgggcggc    480
atggtgcaga ccgtgcagac ccgctacacc ttcggcgccg ccctgttcgt gggctgggtg    540
gccggcggcc tgaccctgat cggcggcgtg atgatgtgca tcgcctgccg cggcctggcc    600
cccgaggaga ccaactacaa ggccgtgagc taccacgcca gcggccacag cgtggcctac    660
aagcccggcg gcttcaaggc cagcaccggc ttcggcagca acaccaagaa caagaagatc    720
tacgacggcg gcgcccgcac cgaggacgag gtgcagagct accccagcaa gcacgactac    780
gtgtaa                                                                786
```

<210> SEQ ID NO 70
<211> LENGTH: 261
<212> TYPE: PRT
<213> ORGANISM: Homo sapiens

<400> SEQUENCE: 70

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 71
<211> LENGTH: 786
<212> TYPE: DNA
<213> ORGANISM: Homo sapiens

<400> SEQUENCE: 71

```
atggccgtga ccgcctgcca gggcctgggc ttcgtggtga gcctgatcgg catcgccggc    60
atcatcgccg ccacctgcat ggaccagtgg agcacccagg acctgtacaa caaccccgtg   120
accgccgtgt tcaactacca gggcctgtgg cgcagctgcg tgcgcgagag cagcggcttc   180
accgagtgcc gcggctactt caccctgctg ggcctgcccg ccatgctgca ggccgtgcgc   240
gccctgatga tcgtgggcat cgtgctgggc gccatcggcc tgctggtgag catcttcgcc   300
ctgaagtgca tccgcatcgg cagcatggag gacagcgcca aggccaacat gaccctgacc   360
agcggcatca tgttcatcgt gagcggcctg tgcgccatcg ccggcgtgag cgtgttcgcc   420
aacatgctgg tgaccaactt ctggatgagc accgccaaca tgtacaccgg catgggcggc   480
atggtgcaga ccgtgcagac ccgctacacc ttcggcgccg ccctgttcgt gggctgggtg   540
gccggcggcc tgaccctgat cggcggcgtg atgatgtgca tcgcctgccg cggcctggcc   600
cccgaggaga ccaactacaa ggccgtgagc taccacgcca gcggccacag cgtggcctac   660
aagcccggcg gcttcaaggc cagcaccggc ttcggcagca caccaagaa caagaagatc    720
tacgacggcg gcgcccgcac cgaggacgag gtgcagagct accccagcaa gcacgactac   780
gtgtaa                                                             786
```

<210> SEQ ID NO 72
<211> LENGTH: 261
<212> TYPE: PRT
<213> ORGANISM: Homo sapiens

<400> SEQUENCE: 72

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220
```

```
Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260
```

<210> SEQ ID NO 73
<211> LENGTH: 261
<212> TYPE: PRT
<213> ORGANISM: Artificial Sequence
<220> FEATURE:
<223> OTHER INFORMATION: Mutant 1

<400> SEQUENCE: 73

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Met Trp Ser Thr
                20                  25                  30

Gln Asp Leu Tyr Asn Asn Pro Val Thr Ala Val Phe Asn Tyr Gln Gly
            35                  40                  45

Leu Trp Arg Ser Cys Val Arg Glu Ser Ser Gly Phe Thr Glu Cys Arg
50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260
```

<210> SEQ ID NO 74
<211> LENGTH: 261
<212> TYPE: PRT
<213> ORGANISM: Artificial Sequence
<220> FEATURE:
<223> OTHER INFORMATION: Mutant 2

<400> SEQUENCE: 74

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asp Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 75
<211> LENGTH: 261
<212> TYPE: PRT
<213> ORGANISM: Artificial Sequence
<220> FEATURE:
<223> OTHER INFORMATION: Mutant 3

<400> SEQUENCE: 75

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ser Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val

```
                        85                  90                  95
Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
            130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
            195                 200                 205

Val Ser Tyr His Ala Ser Gly His Ser Val Ala Tyr Lys Pro Gly Gly
            210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 76
<211> LENGTH: 261
<212> TYPE: PRT
<213> ORGANISM: Artificial Sequence
<220> FEATURE:
<223> OTHER INFORMATION: Mutant 4

<400> SEQUENCE: 76

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Gln Tyr Gln Gly
            35                  40                  45

Leu Trp Arg Ser Cys Val Arg Glu Ser Ser Gly Phe Thr Glu Cys Arg
50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
            85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
            130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
```

180                 185                 190
Cys Ile Ala Cys Arg Gly Leu Ala Pro Glu Glu Thr Asn Tyr Lys Ala
                195                 200                 205

Val Ser Tyr His Ala Ser Gly His Ser Val Ala Tyr Lys Pro Gly Gly
        210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 77
<211> LENGTH: 261
<212> TYPE: PRT
<213> ORGANISM: Artificial Sequence
<220> FEATURE:
<223> OTHER INFORMATION: Mutant 5

<400> SEQUENCE: 77

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Glu Gly
        35                  40                  45

Leu Trp Arg Ser Cys Val Arg Glu Ser Ser Gly Phe Thr Glu Cys Arg
50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

```
<210> SEQ ID NO 78
<211> LENGTH: 261
<212> TYPE: PRT
<213> ORGANISM: Artificial Sequence
<220> FEATURE:
<223> OTHER INFORMATION: Mutant 6

<400> SEQUENCE: 78

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Gln Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 79
<211> LENGTH: 261
<212> TYPE: PRT
<213> ORGANISM: Artificial Sequence
<220> FEATURE:
<223> OTHER INFORMATION: Mutant 7

<400> SEQUENCE: 79

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45
```

```
Leu Trp Arg Ser Cys Val Arg Glu Ser Ser Gly Phe Thr Glu Cys Arg
    50                  55                  60

Pro Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                    85                  90                  95

Ser Ile Phe Ala Leu Lys Cys Ile Arg Ile Gly Ser Met Glu Asp Ser
                100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
                180                 185                 190

Cys Ile Ala Cys Arg Gly Leu Ala Pro Glu Glu Thr Asn Tyr Lys Ala
                195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 80
<211> LENGTH: 261
<212> TYPE: PRT
<213> ORGANISM: Artificial Sequence
<220> FEATURE:
<223> OTHER INFORMATION: Mutant 8

<400> SEQUENCE: 80

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
                20                  25                  30

Gln Asp Leu Tyr Asn Asn Pro Val Thr Ala Val Phe Asn Tyr Gln Gly
            35                  40                  45

Leu Trp Arg Ser Cys Val Arg Glu Ser Ser Gly Phe Thr Glu Cys Arg
    50                  55                  60

Gly Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                    85                  90                  95

Ser Ile Phe Ala Leu Lys Cys Ile Arg Ile Gly Ser Met Glu Asp Ser
                100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
    130                 135                 140
```

```
Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
                195                 200                 205

Val Ser Tyr His Ala Ser Gly His Ser Val Ala Tyr Lys Pro Gly Gly
        210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
                260

<210> SEQ ID NO 81
<211> LENGTH: 261
<212> TYPE: PRT
<213> ORGANISM: Artificial Sequence
<220> FEATURE:
<223> OTHER INFORMATION: Mutant 9

<400> SEQUENCE: 81

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ser Val Phe Gln Tyr Gln Gly
                35                  40                  45

Leu Trp Arg Ser Cys Val Arg Glu Ser Ser Gly Phe Thr Glu Cys Arg
50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
                115                 120                 125

Gly Leu Cys Ala Ile Ala Gly Val Ser Val Phe Ala Asn Met Leu Val
            130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
                195                 200                 205

Val Ser Tyr His Ala Ser Gly His Ser Val Ala Tyr Lys Pro Gly Gly
        210                 215                 220

Phe Lys Ala Ser Thr Gly Phe Gly Ser Asn Thr Lys Asn Lys Lys Ile
225                 230                 235                 240
```

Tyr Asp Gly Gly Ala Arg Thr Glu Asp Glu Val Gln Ser Tyr Pro Ser
            245                 250                 255

Lys His Asp Tyr Val
            260

<210> SEQ ID NO 82
<211> LENGTH: 261
<212> TYPE: PRT
<213> ORGANISM: Artificial Sequence
<220> FEATURE:
<223> OTHER INFORMATION: Mutant 10

<400> SEQUENCE: 82

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ser Val Phe Asn Tyr Glu Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 83
<211> LENGTH: 261
<212> TYPE: PRT
<213> ORGANISM: Artificial Sequence
<220> FEATURE:
<223> OTHER INFORMATION: Mutant 11

<400> SEQUENCE: 83

Met Ala Val Thr Ala Cys Gln Gly Leu Gly Phe Val Val Ser Leu Ile
1               5                   10                  15

```
Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Gln Tyr Glu Gly
                35                  40                  45

Leu Trp Arg Ser Cys Val Arg Glu Ser Ser Gly Phe Thr Glu Cys Arg
 50                  55                  60

Gly Tyr Phe Thr Leu Leu Gly Leu Pro Ala Met Leu Gln Ala Val Arg
 65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
                100                 105                 110

Ala Lys Ala Asn Met Thr Leu Thr Ser Gly Ile Met Phe Ile Val Ser
                115                 120                 125

Gly Leu Cys Ala Ile Ala Gly Val Ser Val Phe Ala Asn Met Leu Val
130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
                180                 185                 190

Cys Ile Ala Cys Arg Gly Leu Ala Pro Glu Glu Thr Asn Tyr Lys Ala
                195                 200                 205

Val Ser Tyr His Ala Ser Gly His Ser Val Ala Tyr Lys Pro Gly Gly
                210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
                260

<210> SEQ ID NO 84
<211> LENGTH: 261
<212> TYPE: PRT
<213> ORGANISM: Artificial Sequence
<220> FEATURE:
<223> OTHER INFORMATION: Mutant 12

<400> SEQUENCE: 84

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ser Val Phe Gln Tyr Glu Gly
                35                  40                  45

Leu Trp Arg Ser Cys Val Arg Glu Ser Ser Gly Phe Thr Glu Cys Arg
 50                  55                  60

Gly Tyr Phe Thr Leu Leu Gly Leu Pro Ala Met Leu Gln Ala Val Arg
 65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
                100                 105                 110
```

```
Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
        130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
        210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 85
<211> LENGTH: 261
<212> TYPE: PRT
<213> ORGANISM: Artificial Sequence
<220> FEATURE:
<223> OTHER INFORMATION: Mutant 13

<400> SEQUENCE: 85

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
        130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205
```

Val Ser Tyr His Ala Ser Gly His Ser Val Ala Tyr Lys Pro Gly Gly
          210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 86
<211> LENGTH: 261
<212> TYPE: PRT
<213> ORGANISM: Artificial Sequence
<220> FEATURE:
<223> OTHER INFORMATION: Mutant 14

<400> SEQUENCE: 86

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Glu Ser Ser Gly Phe Thr Glu Cys Arg
50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 87
<211> LENGTH: 261
<212> TYPE: PRT
<213> ORGANISM: Artificial Sequence
<220> FEATURE:
<223> OTHER INFORMATION: Mutant 15

<400> SEQUENCE: 87

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ala Val Phe Asn Tyr Glu Gly
            35                  40                  45

Leu Trp Arg Ser Cys Val Arg Glu Ser Ser Gly Phe Thr Glu Cys Arg
50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
            130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
            195                 200                 205

Val Ser Tyr His Ala Ser Gly His Ser Val Ala Tyr Lys Pro Gly Gly
            210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 88
<211> LENGTH: 261
<212> TYPE: PRT
<213> ORGANISM: Artificial Sequence
<220> FEATURE:
<223> OTHER INFORMATION: Mutant 16

<400> SEQUENCE: 88

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ala Val Phe Asn Tyr Gln Gly
            35                  40                  45

Leu Trp Arg Ser Cys Val Arg Glu Ser Ser Gly Phe Thr Glu Cys Arg
50                  55                  60

Pro Tyr Phe Thr Ile Leu Gly Leu Pro Ala Met Leu Gln Ala Val Arg

```
              65                  70                  75                  80
Ala Leu Met Ile Val Gly Ile Val Leu Gly Ala Ile Gly Leu Leu Val
                    85                  90                  95

Ser Ile Phe Ala Leu Lys Cys Ile Arg Ile Gly Ser Met Glu Asp Ser
                    100                 105                 110

Ala Lys Ala Asn Met Thr Leu Thr Ser Gly Ile Met Phe Ile Val Ser
                    115                 120                 125

Gly Leu Cys Ala Ile Ala Gly Val Ser Val Phe Ala Asn Met Leu Val
                    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                    165                 170                 175

Val Gly Trp Val Ala Gly Gly Leu Thr Leu Ile Gly Gly Val Met Met
                    180                 185                 190

Cys Ile Ala Cys Arg Gly Leu Ala Pro Glu Glu Thr Asn Tyr Lys Ala
                    195                 200                 205

Val Ser Tyr His Ala Ser Gly His Ser Val Ala Tyr Lys Pro Gly Gly
                    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                    245                 250                 255

Lys His Asp Tyr Val
                260

<210> SEQ ID NO 89
<211> LENGTH: 330
<212> TYPE: PRT
<213> ORGANISM: Artificial Sequence
<220> FEATURE:
<223> OTHER INFORMATION: Mouse IgG2a constant region

<400> SEQUENCE: 89

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                    20                  25                  30

Phe Pro Glu Pro Val Thr Leu Thr Trp Asn Ser Gly Ser Leu Ser Ser
                    35                  40                  45

Gly Val His Thr Phe Pro Ala Val Leu Gln Ser Asp Leu Tyr Thr Leu
                    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                    85                  90                  95

Ile Glu Pro Arg Gly Pro Thr Ile Lys Pro Cys Pro Pro Cys Lys Cys
                    100                 105                 110

Pro Ala Pro Asn Leu Leu Gly Gly Pro Ser Val Phe Ile Phe Pro Pro
                    115                 120                 125

Lys Ile Lys Asp Val Leu Met Ile Ser Leu Ser Pro Ile Val Thr Cys
                    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
```

```
                      165                 170                 175
Glu Asp Tyr Asn Ser Thr Leu Arg Val Val Ser Ala Leu Pro Ile Gln
                180                 185                 190

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
        210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 90
<211> LENGTH: 107
<212> TYPE: PRT
<213> ORGANISM: Artificial Sequence
<220> FEATURE:
<223> OTHER INFORMATION: Mouse kappa constant region

<400> SEQUENCE: 90

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

US 10,421,817 B1

ANTIBODIES BINDING HUMAN CLAUDIN 18.2 AND USES THEREOF

FIELD OF THE INVENTION

The invention relates to an antibody specifically binding to human Claudin 18.2, preparation and use thereof, especially its use in diagnosis, prevention, and treatment of diseases associated with cells expressing Claudin 18.2, including tumors such as pancreatic cancer, gastric cancer, colon cancer, esophageal cancer, hepatic cancer, ovarian cancer, lung cancer and bladder cancer.

BACKGROUND OF THE INVENTION

Cancer and Antibody therapies

Cancer is among the top killer diseases in our society today. According to World Cancer Report 2014, about 14.1 million new cancer cases occur every year, not including skin cancer other than melanoma. Cancers caused about 8.8 million deaths a year (GBL) 2015 Disease and Injury Incidence and Prevalence Collaborators, (2016) Lancet 388 (10053):1545-1602). For example, gastric cancer is the fourth (in males) and fifth (in females) most common causes of cancer-related deaths in the developed countries.

Many cancers, especially those at an advanced stage, remain difficult to cure. For example, the overall five-year survival rate for gastroesophageal cancer is only 20-25%, despite the aggressiveness of the current standard treatment, itself associated with substantial side effects. For pancreatic cancer, patients are usually diagnosed at an advanced stage, so the prognosis is extremely poor, where the median survival time is less than 6 months, and the 5-year survival rate is less than 5.5%.

Antibody therapies are approved in various jurisdictions to treat a wide range of cancers, and have significantly improved patient outcomes (Komeev et al., (2017) Cytokine 89: 127-135). Once bound to a cancer antigen, antibodies may induce antibody-dependent cell-mediated cytotoxicity, activate the complement system, or prevent a receptor from interacting with its ligand, all of which can lead to cancer cell deaths. U.S. FDA-approved antibody drugs include Alemtuzumab, Nivolumab, Rituximab and Durvalumab.

Claudin 18.2

Claudins, first reported by Shorichiro Tsukita et al. in 1998 (Furuse et al., (1998) J Cell Biol 141(7): 1539-1550), are a family of cell-surface proteins that establish a paracellular barrier and control the flow of molecules between cells (Singh et al., (2010) J Oncol 2010: 541957). Claudins are integral components of tight junctions that play important roles in maintaining epithelial cell polarity, controlling paracellular diffusion, and regulating cell growth and differentiation. The other two main tight junction family proteins are occludin and junctional adhesion molecule (JAM). Each claudin molecule spans the cellular membrane 4 times, with the N-terminal and C-terminal ends both located in the cytoplasm.

By now 24 claudin members have been reported in mammals, with Claudin 13 missing in humans. Different claudin members are expressed on different tissues, and their altered functions have been linked to the formation of cancers. Claudin 1, Claudin 18 and Claudin 10 expression level changes have been associated with colon cancer, gastric cancer and hepatocellular carcinoma, respectively, and claudins have thus become promising targets for therapeutic strategies (Swisshelm et al., (2005) Adv Drug Deliv Rev 57(6): 919-928).

Claudin 18, also known as CLD18, has two isoforms. Claudin 18.1 is selectively expressed on normal lung and stomach epithelia. Claudin 18.2 also has a highly restricted expression pattern in normal tissues, limited on the differentiated short-lived cells of stomach epithelium only, and notably absent in the gastric stem cells zone.

Claudin 18.2, however, is abundant in a significant proportion of primary gastric cancers and its metastases, and plays an important role in their malignant transformation. For example, frequent ectopic activation of claudin 18.2 was found in pancreatic, esophageal, ovarian, and lung tumors (Niimi et al., (2001) Mol Cell Biol 21(21): 7380-7390; Tanaka et al. (2011) J Histochem Cytochem 59(10): 942-952; Micke et al., (2014) Int J Cancer 135(9): 2206-2214; Shimobaba et al. (2016) Biochim Biophys Acta 1863(6 Pt A): 1170-1178; Singh et al., (2017) J Hematol Oncol 10(1): 105; Tokumitsu et al., (2017) Cytopathology 28(2): 116-121).

Claudin 18.2 has exposed extracellular loops available for monoclonal antibody binding, and CLDN18.2 antibodies have been used in studies to treat cancers. For example, Claudiximab (IMAB362), a chimeric anti-Claudin 18.2 IgG1 antibody developed by Ganymed, has shown encouraging efficacies in phase 1 and phase 2 clinical trials for treating advanced gastroesophageal cancers (Sahin et al., (2018) Eur J Cancer 100: 17-26).

With the unmet medical needs in many malignancies, there is a need for additional anti-Claudin 18.2 monoclonal antibodies with more desirable pharmaceutical characteristics.

SUMMARY OF THE INVENTION

The present invention provides an isolated monoclonal antibody, for example, a mouse, human, chimeric or humanized monoclonal antibody that binds to Claudin 18.2 (e.g., the human Claudin 18.2, and monkey Claudin 18.2) with higher ADCC activity, CDC activity and/or Claudin 18.2 binding stability compared to prior art antibodies.

The antibody of the invention can be used for a variety of applications, including detection of the Claudin 18.2 protein, and diagnosis, treatment or prevention of Claudin 18.2 related cancers.

Accordingly, in one aspect, the invention pertains to an isolated monoclonal antibody (e.g., a humanized antibody), or an antigen-binding portion thereof, that binds Claudin 18.2, having a heavy chain variable region that comprises a CDR1 region, a CDR2 region and a CDR3 region, wherein the CDR1 region, the CDR2 region and the CDR3 region comprise amino acid sequences having at least 80%, 85%, 90%, 95%, 98%, or 99% identity to, or set forth in
  (1) SEQ ID NOs: 1, 4 and 7, respectively;
  (2) SEQ ID NOs: 2, 4 and 8, respectively;
  (3) SEQ ID NOs: 2, 4 and 9, respectively;
  (4) SEQ ID NOs: 2, 5 and 9, respectively; or
  (5) SEQ ID NOs: 3, 6 and 8, respectively;
wherein, the antibody, or antigen-binding fragment thereof, binds to Claudin 18.2.

In one aspect, an isolated monoclonal antibody, or an antigen-binding portion thereof, of the present invention comprises a heavy chain variable region comprising an amino acid sequence having at least 80%, 85%, 90%, 95%, 98% or 99% identity to, or set forth in SEQ ID NOs: 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49, wherein the antibody or antigen-binding fragment thereof binds to Claudin 18.2.

In one aspect, an isolated monoclonal antibody, or an antigen-binding portion thereof, of the present invention comprises a light chain variable region that comprises a CDR1 region, a CDR2 region and a CDR3 region, wherein the CDR1 region, the CDR2 region, and the CDR3 region comprise amino acid sequences having at least 80%, 85%, 90%, 95%, 98% or 99% identity to, or set forth in
   (1) SEQ ID NOs: 10, 13 and 16, respectively;
   (2) SEQ ID NOs: 11, 13 and 16, respectively;
   (3) SEQ ID NOs: 10, 14 and 16, respectively;
   (4) SEQ ID NOs: 12, 13 and 16, respectively; or
   (5) SEQ ID NOs: 10, 15 and 16, respectively;
wherein the antibody or antigen-binding fragment thereof binds to Claudin 18.2.

In one aspect, an isolated monoclonal antibody, or an antigen-binding portion thereof, of the present invention comprises a light chain variable region comprising an amino acid sequence having at least 80%, 85%, 90%, 95%, 98% or 99% identity to, or set forth in SEQ ID NOs: 50, 51, 52, 53, 54, 55, 56, 57, 58, 59, 60, 61, 62, 63, 64, 65 or 66, wherein the antibody or antigen-binding fragment thereof binds to Claudin 18.2.

In one aspect, an isolated monoclonal antibody, or an antigen-binding portion thereof, of the present invention comprises a heavy chain variable region and a light chain variable region each comprises a CDR1 region, a CDR2 region and a CDR3 region, wherein the heavy chain variable region CDR1, CDR2 and CDR3, and the light chain variable region CDR1, CDR2 and CDR3 comprise amino acid sequences having at least 80%, 85%, 90%, 95%, 98% or 99% identity to, or set forth in (1) SEQ ID NOs: 1, 4, 7, 10, 13 and 16, respectively; (2) SEQ ID NOs: 2, 4, 8, 11, 13 and 16, respectively; (3) 2, 4, 9, 10, 14 and 16, respectively; (4) SEQ ID NOs: 2, 5, 9, 12, 13 and 16, respectively; or (5) SEQ ID NOs: 3, 6, 8, 10, 15 and 16, respectively, wherein the antibody or antigen-binding fragment thereof binds to Claudin 18.2.

In one embodiment, an isolated monoclonal antibody, or the antigen-binding portion thereof, of the present invention comprises a heavy chain variable region and a light chain variable region, the heavy chain variable region and the light chain variable region comprising amino acid sequences having at least 80%, 85%, 90%, 95%, 98% or 99% identity to, or set forth in (1) SEQ ID NOs: 17 and 50, respectively; (2) SEQ ID NOs: 18 and 51, respectively; (3) SEQ ID NOs: 19 and 52, respectively; (4) SEQ ID NOs: 20 and 53, respectively; (5) SEQ ID NOs: 21 and 54, respectively; (6) SEQ ID NOs: 22 and 55, respectively; (7) SEQ ID NOs: 23 and 55, respectively; (8) SEQ ID NOs: 24 and 55, respectively; (9) SEQ ID NOs: 25 and 55, respectively; (10) SEQ ID NOs: 26 and 55, respectively; (11) SEQ ID NOs: 27 and 55, respectively; (12) SEQ ID NOs: 27 and 56, respectively; (13) SEQ ID NOs: 27 and 57, respectively; (14) SEQ ID NOs: 28 and 56, respectively; (15) SEQ ID NOs: 28 and 57, respectively; (16) SEQ ID NOs: 29 and 58, respectively; (17) SEQ ID NOs: 30 and 58, respectively; (18) SEQ ID NOs: 31 and 58, respectively; (19) SEQ ID NOs: 32 and 58, respectively; (20) SEQ ID NOs: 33 and 58, respectively; (21) SEQ ID NOs: 34 and 58, respectively; (22) SEQ ID NOs: 34 and 59, respectively; (23) SEQ ID NOs: 34 and 60, respectively; (24) SEQ ID NOs: 35 and 58, respectively; (25) SEQ ID NOs: 35 and 59, respectively; (26) SEQ ID NOs: 35 and 60, respectively; (27) SEQ ID NOs: 36 and 61, respectively; (28) SEQ ID NOs: 37 and 61, respectively; (29) SEQ ID NOs: 38 and 61, respectively; (30) SEQ ID NOs: 39 and 61, respectively; (31) SEQ ID NOs: 40 and 61, respectively; (32) SEQ ID NOs: 41 and 61, respectively; (33) SEQ ID NOs: 41 and 62, respectively; (34) SEQ ID NOs: 41 and 63, respectively; (35) SEQ ID NOs: 42 and 61, respectively; (36) SEQ ID NOs: 42 and 62, respectively; (37) SEQ ID NOs: 42 and 63, respectively; (38) SEQ ID NOs: 43 and 64, respectively; (39) SEQ ID NOs: 44 and 64, respectively; (40) SEQ ID NOs: 45 and 64, respectively; (41) SEQ ID NOs: 46 and 64, respectively; (42) SEQ ID NOs: 47 and 64, respectively; (43) SEQ ID NOs: 48 and 64, respectively; (44) SEQ ID NOs: 48 and 65, respectively; (45) SEQ ID NOs: 48 and 66, respectively; (46) SEQ ID NOs: 49 and 65, respectively; or (47) SEQ ID NOs: 49 and 66, respectively, wherein the antibody or antigen-binding fragment thereof binds to Claudin 18.2.

In one embodiment, an isolated monoclonal antibody, or the antigen-binding portion thereof, of the present invention comprises a heavy chain and a light chain, the heavy chain comprising a heavy chain variable region and a heavy chain constant region, the light chain comprising a light chain variable region and a light chain constant region, wherein, the heavy chain constant region and the light chain constant region comprise amino acid sequences having at least 80%, 85%, 90%, 95%, 98% or 99% identity to, or set forth in SEQ ID NOs: 67 and 68, respectively, or SEQ ID NOs: 89 and 90, respectively, and the heavy chain variable region and the light chain variable region comprise amino acid sequences described above, wherein the antibody or antigen-binding fragment thereof binds to Claudin 18.2.

The antibody of the present invention in some embodiments comprises or consists of two heavy chains and two light chains, wherein each heavy chain comprises the heavy chain constant region, heavy chain variable region or CDR sequences mentioned above, and each light chain comprises the light chain constant region, light chain variable region or CDR sequences mentioned above, wherein the antibody binds to Claudin 18.2. The antibody of the invention can be a full-length antibody, for example, of an IgG1, IgG2 or IgG4 isotype. The antibody of the present invention in other embodiments may be a single chain antibody, or consists of antibody fragments, such as Fab or Fab'2 fragments.

The antibody, or antigen-binding fragment, of the present invention binds to human Claudin 18.2, and induces antibody-dependent cellular cytotoxicity (ADCC) and complement dependent cytotoxicity (CDC) activity against Claudin 18.2-expressing cells. It does not bind to human Claudin 18.1, and binds to a different human Claudin 18.2 epitope compared to IMAB362. The antibody, or antigen-binding fragment of the present invention has in vivo anti-tumor effect.

The invention also provides an immunoconjugate comprising an antibody of the invention, or antigen-binding portion thereof, linked to a therapeutic agent, such as a cytotoxin. The invention also provides a bispecific molecule comprising an antibody, or antigen-binding portion thereof, of the invention, linked to a second functional moiety (e.g., a second antibody) having a different binding specificity than said antibody, or antigen-binding portion thereof. In another aspect, the antibody or an antigen binding portions thereof of the present invention can be made into part of a chimeric antigen receptor (CAR). The antibody or an antigen binding portions thereof of the present invention can also be encoded by or used in conjuction with an oncolytic virus.

Compositions comprising an antibody, or antigen-binding portion thereof, or immunoconjugate or bispecific molecule of the invention, and a pharmaceutically acceptable carrier, are also provided.

Nucleic acid molecules encoding the antibodies, or antigen-binding portions thereof, of the invention are also encompassed by the invention, as well as expression vectors comprising such nucleic acids and host cells comprising such expression vectors. A method for preparing an anti-Claudin 18.2 antibody using the host cell comprising the expression vector is also provided, comprising steps of (i) expressing the antibody in the host cell and (ii) isolating the antibody from the host cell or its cell culture.

In an aspect, the invention provides a method for diagnosis of a cancer disease in a subject, comprising collecting a tissue sample of interest from the subject, and contacting the tissue sample with the antibody, or antigen-binding portion thereof, of the invention. The subject may be diagnosed with a certain cancer if certain amounts of Claudin 18.2 are detected. The cancer may be a solid tumor, selected form the group consisting of pancreatic cancer, gastric cancer, colon cancer, esophageal cancer, hepatic cancer, ovarian cancer, lung cancer and bladder cancer.

In yet another aspect, the invention provides a method for preventing, treating or ameliorating a cancer disease in a subject, comprising administering to the subject a therapeutically effective amount of the antibody, or antigen-binding portion thereof, of the invention. The cancer may be a solid tumor, selected form the group consisting of pancreatic cancer, gastric cancer, colon cancer, esophageal cancer, hepatic cancer, ovarian cancer, lung cancer and bladder cancer. In some embodiments, the method comprises administering a composition, a bispecific molecule, an immunoconjugate, a CAR-T cell, or an antibody-encoding or antibody-bearing oncolytic virus of the invention. In some embodiments, at least one additional anti-cancer antibody can be administered with the antibody, or an antigen-binding portion thereof, of the invention, such as an anti-PD-1 antibody, an anti-LAG-3 antibody and/or an anti-CTLA-4 antibody. In yet another embodiment, an antibody, or an antigen-binding portion thereof, of the invention is administered with a cytokine (e.g., IL-2 and/or IL-21), or a costimulatory antibody (e.g., an anti-CD137 and/or anti-GITR antibody). In another embodiment, an antibody, or an antigen-binding portion thereof, of the invention is administered with a chemotherapeutic agent, which may be a cytotoxic agent, such as epirubicin, oxaliplatin, and/or 5-fluorouracil (5-FU). The antibodies of the present invention can be, for example, mouse, human, chimeric or humanized antibodies.

In one aspect, the present invention provides a method of treating or preventing a cancer disease in a subject, comprising administering to the subject a therapeutically effective amount of the antibody, or antigen-binding portion thereof, of the invention, in combination with an agent stimulating γδ T cells. The agent stimulating γδ T cells may be administered prior to, simultaneously with or following administration of the antibody, or antigen-binding portion thereof, of the invention. The γδ T cells may be Vγ9Vδ2 T cells. In one embodiment, the agent stimulating γδ T cells is bisphosphonates, in particular nitrogen-containing bisphosphonates, such as N-bisphosphonates and aminobisphosphonates. In one embodiment, the agent stimulating γδ T cells is zoledronic acid, preferably in combination with interleukin-2.

In one embodiment, the cancer disease treatment method of the invention further comprises administering an agent stabilizing or increasing expression of Claudin 18.2. Expression of Claudin 18.2 is preferably at the cell surface of a cancer cell. The agent stabilizing or increasing expression of Claudin 18.2 may be oxaliplatin and/or 5-FU.

Other features and advantages of the instant disclosure will be apparent from the following detailed description and examples, which should not be construed as limiting. The contents of all references, Genbank entries, patents and published patent applications cited throughout this application are expressly incorporated herein by reference.

BRIEF DESCRIPTION OF THE DRAWINGS

FIGS. 11A and 11B show ADCC activity of humanized anti-Claudin 18.2 antibodies against HEK293A cells overexpressing human Claudin 18.1 (A) or human Claudin 18.2 (B).

FIGS. 12A and 12B show CDC activity of humanized anti-Claudin 18.2 antibodies against HEK293A cells overexpressing human Claudin 18.1 (A) or human Claudin 18.2 (B).

FIGS. 17A and 17B show ADCC activity of humanized anti-Claudin 18.2 antibodies against human Claudin 18.2-expressing MC38 cells (A) or NUGC-4 cells (B) by PBMCs.

FIGS. 18A and 18B show ADCC activity of humanized anti-Claudin 18.2 antibodies against human Claudin 18.2-expressing MC38 cells (A) or NUGC-4 cells (B) by Vγ9Vδ2T cells.

FIGS. 19A and 19B show the average tumor volumes (A) and individual tumor weights (B) in groups administered with humanized anti-OX40 antibodies of the invention or control agents, indicating in vivo anti-tumor effect of anti-Claudin 18.2 antibodies.

FIG. 20 shows in vivo anti-tumor effect of anti-Claudin 18.2 antibodies when combined with chemotherapeutic drugs.

FIGS. 21A and 21B show ADCC activity of afucosylated anti-Claudin 18.2 antibodies against EOF pretreated NUGC4 where the afucosylated anti-Claudin 18.2 antibodies were 18F2-30VH0VL0AF (A) and 18F2-35VH7VL3AF (B).

FIGS. 22A and 22B show CDC activity of afucosylated anti-Claudin 18.2 antibodies against human Claudin 18.2-expressing MC38 cells where the afucosylated anti-Claudin 18.2 antibodies were 18F2-30VH0VL0AF (A) and 18F2-35VH7VL3AF (B).

DETAILED DESCRIPTION OF THE INVENTION

Figure 1:
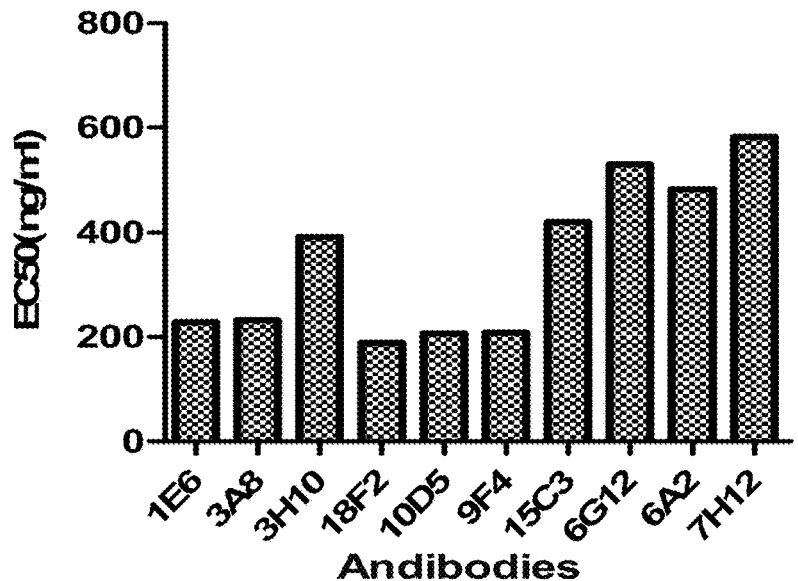
FIG. 1 shows the binding affinity of anti-Claudin 18.2 antibodies to HEK293A cells overexpressing human Claudin 18.2.

To ensure that the present disclosure may be more readily understood, certain terms are first defined. Additional definitions are set forth throughout the detailed description.

The term "Claudin 18.2" refers to Claudin 18, isoform 2. The term "Claudin 18.2" comprises variants, homologs, orthologs and paralogs. For example, an antibody specific for a human Claudin 18.2 protein may, in certain cases, cross-reacts with a Claudin 18.2 protein from a species other than human, such as cynomolgus monkey. In other embodiments, an antibody specific for a human Claudin 18.2 protein may be completely specific for the human Claudin 18.2 protein and exhibit no cross-reactivity to other species or of other types, or may cross-react with Claudin 18.2 from certain other species but not all other species.

The term "human Claudin 18.2" refers to a Claudin 18.2 protein having an amino acid sequence from a human, such as the amino acid sequence having a Genbank accession number of NM_001002026.

The term "antibody" as referred to herein includes whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a Claudin 18.2 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')₂ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (vii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds a Claudin 18.2 protein is substantially free of antibodies that specifically bind antigens other than Claudin 18.2 proteins). An isolated antibody that specifically binds a human Claudin 18.2 protein may, however, have cross-reactivity to other antigens, such as Claudin 18.2 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the invention can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimetic antibody is an antibody having genetic material from a certain species with genetic material from another species.

The term "humanized antibody", as used herein, refers to an antibody from non-human species whose protein sequences have been modified to increase similarity to antibody variants produced naturally in humans.

The phrases "an antibody recognizing an antigen" and "an antibody specific for an antigen" are used interchangeably herein with the term "an antibody which binds specifically to an antigen."

As used herein, an antibody that "specifically binds to human Claudin 18.2" is intended to refer to an antibody that binds to human Claudin 18.2 protein (and possibly a Claudin 18.2 protein from one or more non-human species) but does not substantially bind to non-Claudin 18.2 proteins. Preferably, the antibody binds to human Claudin 18.2 protein with "high affinity"," namely with a $K_D$ of $1.0 \times 10^{-3}$ M or less, and more preferably $5.0 \times 10^{-9}$ M or less.

The term "does not substantially bind" to a protein or cells, as used herein, means does not bind or does not bind with a high affinity to the protein or cells, i.e. binds to the protein or cells with a $K_D$ of $1.0 \times 10^{-6}$ M or more, more preferably $1.0 \times 10^{-5}$ M or more, more preferably $1.0 \times 10^{-4}$ M or more, more preferably $1.0 \times 10^{-3}$ M or more, even more preferably $1.0 \times 10^{-2}$ M or more.

The term "high affinity" for an IgG antibody refers to an antibody having a $K_D$ of $1.0 \times 10^{-6}$ M or less, more preferably $5.0 \times 10^{-8}$ M or less, even more preferably $1.0 \times 10^{-8}$ M or less, even more preferably $5.0 \times 10^{-9}$ M or less and even more preferably $1.0 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$EC_{50}$", also known as half maximal effective concentration, refers to the concentration of an antibody which induces a response halfway between the baseline and maximum after a specified exposure time.

The term "antibody-dependent cellular cytotoxicity", "antibody-dependent cell-mediated cytotoxicity" or "ADCC," as used herein, refers to a mechanism of cell-mediated immune defense whereby an effector cell of the immune system actively lyses a target cell, such as a tumor cell, whose membrane-surface antigens have been bound by antibodies such as anti-Claudin 18.2 antibodies.

The term "complement-dependent cytotoxicity" or "CDC" generally refers to an effector function of IgG and IgM antibodies, which trigger classical complement pathway when bound to a surface antigen, inducing formation of a membrane attack complex and target cell lysis. The antibody of the present invention, by binding to Claudin 18.2, induces CDC against cancer cells.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody of the present invention sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

The term "γδ T cell" refers to T cells whose T cell receptor consists of one γ chain and one δ chain. Human γδ T cells play an important role in stress-surveillance responses in infectious diseases, autimmunity, and transformation-induced changes in tumors. Activated γδ T cells at lesional sites, upon antigen engagement, provide cytokines and/or chemokines mediating recruitment of other effector cells and show immediate effector functions such as ADCC. Most γδ T cells in peripheral blood express Vγ9Vδ2 T cell receptor and are referred to as Vγ9Vδ2 T cells.

The term "agent stimulating γδ T cells" refers to compounds stimulating development of γδ T cells, in particular Vγ9Vδ2 T cells, in vitro and/or in vivo, in particular by inducing activation and expansion of γδ T cells. Preferably, the term relates to compounds, which in vitro and/or in vivo increase isopentenyl pyrophosphate (IPP) produced in mammalian cells, preferably by inhibiting the mevalonate pathway enzyme farnesyl pyrophosphate synthase (FPPS).

Various aspects of the invention are described in further detail in the following subsections.

Anti-Claudin 18.2 Antibodies Having Binding Specificity to Human Claudin 18.2 and Advantageous Functional Properties Antibodies of the invention specifically bind to human Claudin 18.2 with high affinity. In particular, antibodies of the invention bind to human Claudin 18.2 proteins with an $EC_{50}$ value comparable with that of IMAB362, but have higher ADCC activity, CDC activity and/or Claudin 18.2 binding stability. Antibodies of the invention bind to epitopes different from that for IMAB362, and do not bind to Claudin 18.1.

Preferred antibodies of the invention are monoclonal antibodies. Additionally or alternatively, the antibodies can be, for example, mouse, chimeric or humanized monoclonal antibodies.

Monoclonal Anti-Claudin 18.2 Antibody

A preferred antibody of the invention is the monoclonal antibody structurally and chemically characterized as described below and in the following Examples. The $V_H$ amino acid sequence of the anti-Claudin 18.2 antibody is set forth in SEQ ID NOs: 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49. The $V_L$ amino acid sequence of the anti-Claudin 18.2 antibody is shown in SEQ ID NOs: 50, 51, 52, 53, 54, 55, 56, 57, 58, 59, 60, 61, 62, 63, 64, 65 or 66. The amino acid sequences of the heavy/light chain variable regions of the antibodies are summarized in Table 1 below, some clones sharing the same $V_H$ or $V_L$. The amino acid sequences of the heavy chain constant region and the light chain constant region for all clones are set forth in SEQ ID NOs: 67 and 68, respectively, or alternatively SEQ ID NOs.:89 and 90, respectively.

anti-Claudin 18.2 antibody, wherein the antibody specifically binds human Claudin 18.2.

In another embodiment, an antibody of the invention, or an antigen binding portion thereof, comprises:

TABLE 1

Amino acid SEQ ID NOs. of heavy/light chain variable regions

| Clone | SEQ ID NO. | | | | | | | |
|---|---|---|---|---|---|---|---|---|
| | HV-CDR1 | HV-CDR2 | HV-CDR3 | HV | LV-CDR1 | LV-CDR2 | LV-CDR3 | LV |
| 18F2 | 1 | 4 | 7 | 17 | 10 | 13 | 16 | 50 |
| 18F2-5 | 2 | 4 | 8 | 18 | 11 | 13 | 16 | 51 |
| 18F2-30 | 2 | 4 | 9 | 19 | 10 | 14 | 16 | 52 |
| 18F2-35 | 2 | 5 | 9 | 20 | 12 | 13 | 16 | 53 |
| 18F2-66 | 3 | 6 | 8 | 21 | 10 | 15 | 16 | 54 |
| 18F2-5VH0VL0 | 2 | 4 | 8 | 22 | 11 | 13 | 16 | 55 |
| 18F2-5VH2VL0 | 2 | 4 | 8 | 23 | 11 | 13 | 16 | 55 |
| 18F2-5VH3VL0 | 2 | 4 | 8 | 24 | 11 | 13 | 16 | 55 |
| 18F2-5VH4VL0 | 2 | 4 | 8 | 25 | 11 | 13 | 16 | 55 |
| 18F2-5VH5VL0 | 2 | 4 | 8 | 26 | 11 | 13 | 16 | 55 |
| 18F2-5VH6VL0 | 2 | 4 | 8 | 27 | 11 | 13 | 16 | 55 |
| 18F2-5VH6VL2 | 2 | 4 | 8 | 27 | 11 | 13 | 16 | 56 |
| 18F2-5VH6VL3 | 2 | 4 | 8 | 27 | 11 | 13 | 16 | 57 |
| 18F2-5VH7VL2 | 2 | 4 | 8 | 28 | 11 | 13 | 16 | 56 |
| 18F2-5VH7VL3 | 2 | 4 | 8 | 28 | 11 | 13 | 16 | 57 |
| 18F2-30-VH0VL0 | 2 | 4 | 9 | 29 | 10 | 14 | 16 | 58 |
| 18F2-30-VH2VL0 | 2 | 4 | 9 | 30 | 10 | 14 | 16 | 58 |
| 18F2-30-VH3VL0 | 2 | 4 | 9 | 31 | 10 | 14 | 16 | 58 |
| 18F2-30-VH4VL0 | 2 | 4 | 9 | 32 | 10 | 14 | 16 | 58 |
| 18F2-30-VH5VL0 | 2 | 4 | 9 | 33 | 10 | 14 | 16 | 58 |
| 18F2-30-VH6VL0 | 2 | 4 | 9 | 34 | 10 | 14 | 16 | 58 |
| 18F2-30-VH7VL0 | 2 | 4 | 9 | 35 | 10 | 14 | 16 | 58 |
| 18F2-30-VH6VL2 | 2 | 4 | 9 | 34 | 10 | 14 | 16 | 59 |
| 18F2-30-VH6VL3 | 2 | 4 | 9 | 34 | 10 | 14 | 16 | 60 |
| 18F2-30-VH7VL2 | 2 | 4 | 9 | 35 | 10 | 14 | 16 | 59 |
| 18F2-30-VH7VL3 | 2 | 4 | 9 | 35 | 10 | 14 | 16 | 60 |
| 18F2-35-VH0VL0 | 2 | 5 | 9 | 36 | 12 | 13 | 16 | 61 |
| 18F2-35VH2VL0 | 2 | 5 | 9 | 37 | 12 | 13 | 16 | 61 |
| 18F2-35VH3VL0 | 2 | 5 | 9 | 38 | 12 | 13 | 16 | 61 |
| 18F2-35VH4VL0 | 2 | 5 | 9 | 39 | 12 | 13 | 16 | 61 |
| 18F2-35VH5VL0 | 2 | 5 | 9 | 40 | 12 | 13 | 16 | 61 |
| 18F2-35VH6VL0 | 2 | 5 | 9 | 41 | 12 | 13 | 16 | 61 |
| 18F2-35VH7VL0 | 2 | 5 | 9 | 42 | 12 | 13 | 16 | 61 |
| 18F2-35VH6VL2 | 2 | 5 | 9 | 41 | 12 | 13 | 16 | 62 |
| 18F2-35VH6VL3 | 2 | 5 | 9 | 41 | 12 | 13 | 16 | 63 |
| 18F2-35VH7VL2 | 2 | 5 | 9 | 42 | 12 | 13 | 16 | 62 |
| 18F2-35VH7VL3 | 2 | 5 | 9 | 42 | 12 | 13 | 16 | 63 |
| 18F2-66VH0VL0 | 3 | 6 | 8 | 43 | 10 | 15 | 16 | 64 |
| 18F2-66VH2VL0 | 3 | 6 | 8 | 44 | 10 | 15 | 16 | 64 |
| 18F2-66VH3VL0 | 3 | 6 | 8 | 45 | 10 | 15 | 16 | 64 |
| 18F2-66VH4VL0 | 3 | 6 | 8 | 46 | 10 | 15 | 16 | 64 |
| 18F2-66VH5VL0 | 3 | 6 | 8 | 47 | 10 | 15 | 16 | 64 |
| 18F2-66VH6VL0 | 3 | 6 | 8 | 48 | 10 | 15 | 16 | 64 |
| 18F2-66VH6VL2 | 3 | 6 | 8 | 48 | 10 | 15 | 16 | 65 |
| 18F2-66VH6VL3 | 3 | 6 | 8 | 48 | 10 | 15 | 16 | 66 |
| 18F2-66VH7VL2 | 3 | 6 | 8 | 49 | 10 | 15 | 16 | 65 |
| 18F2-66VH7VL3 | 3 | 6 | 8 | 49 | 10 | 15 | 16 | 66 |

The $V_H$ and/or $V_L$ sequences (or CDR sequences) of other anti-Claudin 18.2 antibodies which bind to human Claudin 18.2 can be "mixed and matched" with the $V_H$ and/or $V_L$ sequences (or CDR sequences) of the anti-Claudin 18.2 antibody of the present invention. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the invention, or an antigen binding portion thereof, comprises:
(a) a heavy chain variable region comprising an amino acid sequence listed above in Table 1; and
(b) a light chain variable region comprising an amino acid sequence listed above in Table 1, or the $V_L$ of another (a) the CDR1, CDR2, and CDR3 regions of the heavy chain variable region listed above in Table 1; and
(b) the CDR1, CDR2, and CDR3 regions of the light chain variable region listed above in Table 1 or the CDRs of another anti-Claudin 18.2 antibody, wherein the antibody specifically binds human Claudin 18.2.

In yet another embodiment, the antibody, or antigen binding portion thereof, includes the heavy chain variable CDR2 region of anti-Claudin 18.2 antibody combined with CDRs of other antibodies which bind human Claudin 18.2, e.g., CDR1 and/or CDR3 from the heavy chain variable region, and/or CDR1, CDR2, and/or CDR3 from the light chain variable region of a different anti-Claudin 18.2 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on the CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: *Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

In another embodiment, antibodies of the invention comprise the CDR2 of the heavy chain variable region of the anti-Claudin 18.2 antibody and at least the CDR3 of the heavy and/or light chain variable region of the anti-Claudin 18.2 antibody, or the CDR3 of the heavy and/or light chain variable region of another anti-Claudin 18.2 antibody, wherein the antibody is capable of specifically binding to human Claudin 18.2. These antibodies preferably (a) compete for binding with Claudin 18.2; (b) retain the functional characteristics; (c) bind to the same epitope; and/or (d) have a similar binding affinity as the anti-Claudin 18.2 antibody of the present invention. In yet another embodiment, the antibodies further may comprise the CDR2 of the light chain variable region of the anti-Claudin 18.2 antibody, or the CDR2 of the light chain variable region of another anti-Claudin 18.2 antibody, wherein the antibody is capable of specifically binding to human Claudin 18.2. In another embodiment, the antibodies of the invention may include the CDR1 of the heavy and/or light chain variable region of the anti-Claudin 18.2 antibody, or the CDR1 of the heavy and/or light chain variable region of another anti-Claudin 18.2 antibody, wherein the antibody is capable of specifically binding to human Claudin 18.2.

Conservative Modifications

In another embodiment, an antibody of the invention comprises a heavy and/or light chain variable region sequences of CDR1, CDR2 and CDR3 sequences which differ from those of the anti-Claudin 18.2 antibodies of the present invention by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises a sequence listed in Table 1 above, and/or conservative modifications thereof; and/or (b) the heavy chain variable region CDR2 sequence comprises a sequence listed in Table 1 above, and conservative modifications thereof; and/or (c) the heavy chain variable region CDR3 sequence comprises a sequence listed in Table 1 above, and conservative modifications thereof; and/or (d) the light chain variable region CDR1, and/or CDR2, and/or CDR3 sequences comprise the sequence(s) listed in Table 1 above; and/or conservative modifications thereof; and (e) the antibody specifically binds human Claudin 18.2.

The antibody of the present invention possesses one or more of the following functional properties described above, such as high affinity binding to human Claudin 18.2, and the ability to induce ADCC or CDC activity against Claudin 18.2-expressing cells.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Engineered and Modified Antibodies

Antibodies of the invention can be prepared using an antibody having one or more of the $V_H/V_L$ sequences of the anti-Claudin 18.2 antibody of the present invention as starting material to engineer a modified antibody. An antibody can be engineered by modifying one or more residues within one or both variable regions (i.e., $V_H$ and/or $V_L$), for example within one or more CDR regions and/or within one or more framework regions, to improve binding affinity and/or increase similarity to antibody variants produced naturally in certain animal species. For example, the framework regions are modified to provide humanized antibodies. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad.* See also U.S.A. 86:10029-10033; U.S. Pat. Nos. 5,225,539; 5,530,101; 5,585,089; 5,693,762 and 6,180,370).

Accordingly, another embodiment of the invention pertains to an isolated monoclonal antibody, or antigen binding portion thereof, comprising a heavy chain variable region comprising CDR1, CDR2, and CDR3 sequences comprising the sequences of the present invention, as described above, and/or a light chain variable region comprising CDR1, CDR2, and CDR3 sequences comprising the sequences of the present invention, as described above. While these antibodies contain the $V_H$ and $V_L$ CDR sequences of the monoclonal antibody of the present invention, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the invention are those that are structurally similar to the framework sequences used by antibodies of the invention. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the invention provides isolated anti-Claudin 18.2 monoclonal antibodies, or antigen binding portions thereof, comprising a heavy chain variable region and a light chain variable region comprising: (a) a $V_H$ CDR1 region comprising the sequence of the present invention, or an amino acid sequence having one, two, three, four or five amino acid substitutions, deletions or additions; (b) a $V_H$ CDR2 region comprising the sequence of the present invention, or an amino acid sequence having one, two, three, four or five amino acid substitutions, deletions or additions; (c) a $V_H$ CDR3 region comprising the sequence of the present invention, or an amino acid sequence having one, two, three, four or five amino acid substitutions, deletions or additions; (d) a $V_L$ CDR1 region comprising the sequence of the present invention, or an amino acid sequence having one, two, three, four or five amino acid substitutions, deletions or additions; (e) a $V_L$ CDR2 region comprising the sequence of the present invention, or an amino acid sequence having one, two, three, four or five amino acid substitutions, deletions or additions; and (f) a $V_L$ CDR3 region comprising the sequence of the present invention, or an amino acid sequence having one, two, three, four or five amino acid substitutions, deletions or additions.

Engineered antibodies of the invention include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, an aglycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 ($\alpha(1,6)$-fucosyltransferase), such that antibodies expressed in the Ms704, Ms705, and Ms709 cell lines lack fucose on their carbohydrates. The Ms704, Ms705, and Ms709 FUT8-/- cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277: 26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. PCT Publication WO 99/54342 describes cell lines engineered to express glycoprotein-modifying glycosyl transferases (e.g., $\beta(1,4)$-N-acetylglucosaminyltransferase III (GnTIII)) such that antibodies expressed in the engineered cell lines exhibit increased bisecting GlcNac structures which results in increased ADCC activity of the antibodies (see also Umana et al., (1999) Nat. Biotech. 17:176-180). Alternatively, the fucose residues of the antibody can be cleaved off using a fucosidase enzyme; e.g., the fucosidase $\alpha$-L-fucosidase removes fucosyl residues from antibodies (Tarentino et al., (1975) Biochem. 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EPO 154 316 and EP 0 401 384.

Antibody's Physical Properties

Antibodies of the invention can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al., (2000) Mol Immunol 37:697-706). Glycosylation has been known to occur at motifs containing an N-X-S/T sequence. In some instances, it is preferred to have an anti-Claudin 18.2 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-Claudin 18.2 antibody that contains a pI value that falls in the normal range. This can be achieved either by selecting antibodies with a pI in the normal range or by mutating charged surface residues.

Nucleic Acid Molecules Encoding Antibodies of the Invention

In another aspect, the invention provides nucleic acid molecules that encode heavy and/or light chain variable regions, or CDRs, of the antibodies of the invention. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the invention can be, e.g., DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the invention include those encoding the $V_H$ and $V_L$ sequences of the Claudin 18.2 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) Science 242:423-426; Huston et al., (1988) Proc. Natl. Acad. Sci. USA 85:5879-5883; McCafferty et al., (1990) Nature 348:552-554).

Production of Monoclonal Antibodies of the Invention

Monoclonal antibodies (mAbs) of the present invention can be produced using the well-known somatic cell hybridization (hybridoma) technique of Kohler and Milstein (1975) Nature 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

Antibodies of the invention can be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051, 081; WO 07/059,404; WO 08/083,312; and WO 08/103,693; U.S. Patent Publications 20060024317; 20060004081; and 20060247295; the disclosures of which are incorporated herein by reference.

Bispecific Molecules

In another aspect, the present disclosure features bispecific molecules comprising one or more antibodies of the invention linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-Claudin 18.2 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, CD40, or ICAM-1) or other immune cell, resulting in an increased immune response against the target cell.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv)2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

Antibody-Encoding or Antibody-Bearing Oncolytic Virus

An oncolytic virus preferentially infects and kills cancer cells. Antibodies of the present invention can be used in conjunction with oncolytic viruses. Alternatively, oncolytic viruses encoding antibodies of the present invention can be introduced into human body.

Pharmaceutical Compositions

In another aspect, the present disclosure provides a pharmaceutical composition comprising one or more antibodies of the present invention formulated together with a pharmaceutically acceptable carrier. The composition may optionally contain one or more additional pharmaceutically active ingredients, such as another antibody or a drug. The pharmaceutical compositions of the invention also can be administered in a combination therapy with, for example, another anti-cancer agent, another anti-inflammatory agent, or a vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the antibody, the dosage may range from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-Claudin 18.2 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/ml and in some methods about 25-300 µg/ml.

A "therapeutically effective dosage" of an anti-Claudin 18.2 antibody of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the invention can be formulated to ensure proper distribution in vivo. For example, to ensure that the therapeutic antibody of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett* 346:123; and Killion and Fidler (1994) *Immunomethods* 4:273.

Uses and Methods of the Invention

Antibodies (compositions, bispecifics, and immunoconjugates) of the present invention have numerous in vitro and in vivo utilities involving, for example, diagnosis, treatment and/or prognosis of cancers. The antibodies can be administered to human subjects, e.g., in vivo, to inhibit tumor growth. In diagnosis and prognosis of cancers, a tissue sample of interest can be collected and made contact with the antibodies of the invention, wherein a subject may be diagnosed with cancer if certain amounts of Claudin 18.2 are detected in certain areas or cell types, and increase/decrease of Claudin 18.2 expression indicates cancer development/amelioration.

Given the ability of anti-Claudin 18.2 antibodies of the invention to inhibit proliferation and survival of cancer cells, the invention provides methods for inhibiting growth of tumor cells in a subject comprising administering to the subject an antibody of the invention such that growth of the tumor is inhibited in the subject. Non-limiting examples of tumors that can be treated by antibodies of the invention include, but not limited to, pancreatic cancer, gastric cancer, colon cancer, esophageal cancer, hepatic cancer, ovarian cancer, lung cancer and bladder cancer, original and/or metastatic. Additionally, refractory or recurrent malignancies whose growth may be inhibited using the antibodies of the invention.

These and other methods of the invention are discussed in further detail below.

Combination Therapy

In another aspect, the invention provides methods of combination therapy in which an anti-Claudin 18.2 antibody (or antigen-binding portion thereof) of the present invention is co-administered with one or more additional antibodies that are effective in inhibiting tumor growth in a subject. In one embodiment, the invention provides a method for inhibiting tumor growth in a subject comprising administering to the subject an anti-Claudin 18.2 antibody and one or more additional antibodies, such as an anti-LAG-3 antibody, an anti-PD-1 antibody and/or an anti-CTLA-4 antibody. In certain embodiments, the subject is human. In another aspect, the invention provides cancer treatment methods in which an anti-Claudin 18.2 antibody (or antigen-binding portion thereof) of the present invention is co-administered with a chemotherapeutic agent, which may be a cytotoxic agent. For example, epitubicin, oxaliplatin, and/or 5-FU can be administered to patients receiving anti-Claudin 18.2 therapy. Oxaliplatin and 5-FU are believed to stabilize or increase Claudin 18.2 expression.

The present invention also provides a method for inhibiting tumor growth in a subject comprising administering to the subject an anti-Claudin 18.2 antibody and an agent stimulating γδ T cells, particularly Vγ9Vδ2 T cells. The agent stimulating γδ T cells can be bisphosphonates, in particular nitrogen-containing bisphosphonates, such as N-bisphosphonates and aminobisphosphonates. Data shows that zoledronic acid (ZA), in particular when administered in conjunction with recombinant interleukin-2 (IL-2), stimulates γδ T cells and accordingly augments the ADCC activity of an anti-Claudin 18.2 antibody (WO2013174509).

The present invention also provides a method for inhibiting tumor growth in a subject comprising administering to the subject an anti-Claudin 18.2 antibody and an agent stabilizing or increasing expression of Claudin 18.2. The agent stabilizing or increasing expression of Claudin 18.2 may be a cytotoxic and/or cytostatic agent. The agent stabilizing or increasing expression of Claudin 18.2 may comprise an agent selected from the group consisting of anthracyclines, platinum compounds, nucleoside analogs, taxanes, and camptothecin analogs, or prodrugs thereof, and combinations thereof. The agent stabilizing or increasing expression of Claudin 18.2 may comprise an agent selected from the group consisting of epirubicin, oxaliplatin, cisplatin, 5-fluorouracil. The agent stabilizing or increasing expression of Claudin 18.2 may comprise a combination of oxaliplatin and 5-fluorouracil or prodrugs thereof, a combination of cisplatin and 5-fluorouracil or prodrugs thereof, a combination of at least one taxane and oxaliplatin, a combination of at least one taxane and 5-fluorouracil or prodrugs thereof, or a combination of at least one camptothecin analog and 5-fluorouracil or prodrugs thereof. The agent stabilizing or increasing expression of Claudin 18.2 may be an agent inducing immunogenic cell death. The agent inducing immunogenic cell death may comprise an agent selected from the group consisting of anthracyclines, oxaliplatin and combinations thereof. The agent stabilizing or increasing expression of Claudin 18.2 may comprise a combination of epirubicin and oxaliplatin. In one embodiment, the method of the invention comprises administering at least one anthracycline, at least one platinum compound and at least one of 5-fluorouracil and prodrugs thereof. The anthracycline may be selected from the group consisting of epirubicin, doxorubicin, daunorubicin, idarubicin and valrubicin. Preferably, the anthracycline is epirubicin. The platinum compound may selected from the group consisting of oxaliplatin and cisplatin. The nucleoside analog may be selected from the group consisting of 5-fluorouracil and prodrugs thereof. The taxane may be selected from the group consisting of docetaxel and paclitaxel. The camptothecin analog may be selected from the group consisting of irinotecan and topotecan. In one embodiment, the method of the invention comprises administering (i) epirubicin, oxaliplatin and 5-fluorouracil, (ii) epirubicin, oxaliplatin and capecitabine, (iii) epirubicin, cisplatin and 5-fluorouracil, (iv) epirubicin, cisplatin and capecitabine, or (v) folinic acid, oxaliplatin and 5-fluorouracil.

Other therapies that may be combined with anti-Claudin 18.2 antibody includes, but not limited to immunogenic agent administration, interleukin-2 (IL-2) administration, radiation, surgery, or hormone deprivation.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Construction of HEK293A Cell Lines Stably Expressing Human Claudin 18.1 or Claudin 18.2

HEK293A cells (Cobioer, China) overexpressing human Claudin 18.1 or Claudin 18.2 were generated by using the lentivirus transfection system. Briefly, cDNA sequences (SEQ ID NOs: 69 and 71) encoding human Claudin 18.1 (SEQ ID NO: 70) and Claudin 18.2 (SEQ ID NO: 72) were synthesized and cloned into pLV-EGFP(2A)-Puro plasmids, respectively, at EcoRI and BamHI sites. Lentiviruses were generated in HEK-293T (Cobioer, China) cells by cotransfection with pLV-EGFP(2A)-Puro-Claudin 18.1 (or pLV-EGFP(2A)-Puro-Claudin 18.2), psPAX2 and pMD2.G plasmids. The obtained lentiviruses were used to infect the HEK293A cells to generate stable cell lines overexpressing human Claudin 18.1 or Claudin 18.2, which were then cultured in DMEM medium (Cat #: SH30022.01, Gibco)

with 10% FBS (Cat #: FND500, Excell) and 0.2 μg/ml puromycin (Cat #: A11138-03, Gibco) for more than 7 days.

The expression of Claudin 18.1 or Claudin 18.2 was confirmed by fluorescence-activated cell sorting (FACS) using the commercially available anti-CLDN18 antibody (rabbit anti-Claudin-18, Cat #: 388100, Life Technology). Briefly, 100,000 transfected cells were seeded into each well of 96-well plates, to which anti-human Claudin 18 antibodies were added later. After incubated at 4° C. for 1 hour, plates were washed 3 times with PBST. Then, a PE coupled donkey anti-rabbit IgG secondary antibody (PE Donkey anti-rabbit IgG Antibody, Cat #: 406421, Biolegend) diluted 500× was added to the plates. After incubation at 4° C. for 1 hour, plates were washed with PBS for 3 times and then the cell fluorescence was monitored using a FACS machine (BD).

Example 2 Generation and Screening of Anti-Claudin 18.2 Monoclonal Antibodies

To generate monoclonal antibodies binding human Claudin 18.2, six-week old BALB/c mice were inoculated with the HEK293A cells stably expressing human Claudin 18.2 (see Example 1). Briefly, mice were subcutaneously injected with $2 \times 10^7$/ml HEK293A/human Claudin 18.2 cells followed by three boosts in a four-week-interval. Antibody titers in the serum samples were determined by FACS using the HEK293A cells expressing human Claudin 18.2. When the animals reached suitable antibody titers, the mice were given a final immunization boost with $5 \times 10^7$/mL cells in PBS. Three days later, the mice were euthanized, exsanguinated, and the spleens were harvested for mRNA extraction and phage display library construction.

To construct a scFv phage display library, the total spleen RNAs of the mice were extracted using Trizol kit (Invitrogen), and cDNAs were synthesized using Reverse Transcriptase Kit (Invitrogen). Gene amplification was done by PCR using the cDNA synthesized above as templates, and the scFv phase library was constructed using a proprietary phagemid, pTGS. Briefly, the variable region of light chain was amplified by PCR, purified using Qiagen PCR/purification kit, digested with restriction enzymes NheI and NotI (NEB), and then ligated into the NheI/NotI restriction site of phagemid pTGS (digested with the same restriction enzymes and purified by agarose gel) at 16° C. Following ligation, the recombinant DNA was precipitated, washed and dissolved in distilled water. The recombinant DNA was then transformed into *E. coli* TG1 cells by electroporation. Then, the cells were suspended in 10 ml of SOC medium, and cultured for 1 h at 37° C. with gentle shaking. The cell culture was plated on 2YT agar/ampicillin and the number of ampicillin resistant colonies was counted. For cloning of the variable fragments of the heavy chains, the PCR product was digested with NcoI and XhoI and was ligated into the light chain variable region library and transformed into *E. coli* TG1. The library was scraped from the large plate, and inoculated to 2YTAG liquid culture media. Approximately $10^{12}$ pfu helper phages were added to TG1 samples containing scFv gene libraries and incubated for 1 h at 37° C. with shaking. Seventy μg/ml of Kanamycin was added and the culture was shaken overnight at 30° C. The cells were centrifuged at 4000 rpm for 15 min at 4° C. The resultant supernatant was mixed with 5 ml of 20% PEG 8000/2.5 M NaCl and incubated on ice for 30 min, and then the phages were precipitated by centrifugation at 8000 rpm for 20 min at 4° C. The phages were resuspended in 1.5 ml of PBS containing 1% BSA, vortexed and centrifuged at 13000 rpm for 5 min to pellet debris. The supernatant was stored at 4° C. or used directly for the biopanning (see below).

Antibodies against human Claudin 18.2 but not human Claudin 18.1 were selected by biopanning using HEK293A cells stably expressing human Claudin 18.2 or Claudin 18.1. Briefly, $1 \times 10^7$ HEK293A/human claudin 18.1 cells were firstly added to a 15 ml tube containing $10^{13}$ phages. The cell/phage mixture was incubated for 90 min at room temperature on a shaker, and then was kept without shaking for another 30 min. The cell suspension was centrifuged at 1000 g for 5 min at room temperature and then the supernatant was transferred to a tube containing $1 \times 10^7$ HEK293A/human claudin 18.2 cells. The cell culture was incubated on a shaker for 2 h at room temperature. Unbound phages were washed away using PBS and then 0.1M Glycine-HCl (pH2.2) was used to elute antigen bound phages. Eluted phage was neutralized to pH 7.0 using 1.5M Tris-HCl (pH8.8). The above neutralized phages were used to infect 10 ml of TG1 bacteria, which were cultured at 37° C. until OD reached 0.6. The bacteria culture was pelleted by centrifugation and the pellet was resuspended in culture media, which was coated on a large 2YTAG plate for the next round of screening. Three rounds of such enrichment and screening were carried out in total.

After three rounds of biopanning, phages binding to Claudin 18.2 were collected and used to infect bacterial cells. Single bacterial colonies were picked up and grown in 96-well plates. Cell-based ELISA was used to identify high binders using HEK293A cells expressing human Claudin 18.2 or Claudin 18.1. Clones showing high binding capacity specifically to human Claudin 18.2 but not to Claudin 18.1 in phage ELISA were selected and then subjected to DNA sequencing, and 38 readable scFv sequences were identified from high binding clones, from which 10 scFv antibodies were selected for further characterizations.

Example 3 Expression, Purification and Characterization of Full Length Anti-Claudin 18.2 Monoclonal Antibodies Ten selected scFv antibodies were expressed in HEK293F (Cobioer, China) cells as full length monoclonal antibodies for further characterization. Briefly, the expression vectors were constructed by cloning respective heavy/light chain variable region plus the human IgG1/kappa constant regions (SEQ ID Nos.: 67 and 68) into EcoRI/BamHI of pCDNA3.1 (Invitrogen, Carlsbad, USA).

Chimeric anti-human Claudin 18.2 antibodies were transiently expressed in HEK-293F cells using PEI transfection according to the manufacturer's manual. Briefly, HEK-293F cells were transfected with the resulting vectors using polyethyleneinimine (PEI) at a DNA:PEI ratio of 1:3. Total DNA used per transfection was 1.5 μg/ml. Transfected HEK-293F cells were cultured in an incubator in 5% $CO_2$ at 37° C. with shaking at 120 RPM. After 10-12 days, supernatants were harvested and monoclonal antibodies were purified. Briefly, the cell cultures were collected, followed by centrifugation at 3500 rpm for 5 minutes and then subject to filtration using a 0.22 μm capsule to remove the cell debris. Monoclonal antibodies were then purified using a pre-equilibrated Protein-A affinity column (GE; USA; Cat#: 17040501; Lot#: 10252250) and eluted with the elution buffer (20 mM citric acid, pH3.0-3.5). After buffer exchange, antibodies were kept in PBS buffer (pH 7.0) and their concentrations were determined using a NanoDrop instrument. The purified monoclonal antibodies were subjected to further characterizations.

Ten full length anti-Claudin 18.2 antibodies were then tested for the binding affinity and specificity by FACS using HEK293A cells expressing human Claudin 18.2 or Claudin 18.1. It was shown that most of the full length antibodies specifically bound to human Claudin 18.2 but not to human Claudin 18.1, as shown in FIG. 1. Based on the ranking of the binding affinity, 18F2 were selected for further investigations.

Example 4 Affinity Maturation of 18F2 by Phage Display

To further improve the binding affinity, clone 18F2 was selected for affinity maturation by phage display techniques. Briefly, three-dimensional structural modeling simulation was performed to identify potential residues in the heavy and light chain CDRs of clone 18F2 that might be important for binding affinity. The CDR residues identified were subject to mutagenesis by PCRs using specially designed primers and standard protocol for site-directed mutagenesis. A phage display library was then constructed and then subjected to biopanning as described above using the HEK293A cells stably expressing human Claudin 18.2 or Claudin 18.1. After 3 rounds of biopanning, the high binders were selected, harvested and then used to infect bacterial cells. Bacterial colonies were picked up and grown onto 96-well plates and cell-based ELISA was then used to identify the high binders which were sequenced later. The beneficial mutations in the heavy and light chain CDRs were identified and then combined into a new phage display library, which were subject to another 3 rounds of biopanning and sequencing confirmation as described above. Over 20 high binders were identified which contained from single to multiple mutations as compared to their parent clone 18F2 and 12 clones were selected to be expressed in HEK293F cells as full length, chimeric human IgG1/kappa antibodies. The binding affinity of the full length antibodies were tested by FACS using HEK293 cells expressing human Claudin 18.2 or human Claudin 18.1. Briefly, 100,000 cells were seeded into each well of the 96-well plates and serially diluted anti-Claudin 18.2 antibodies were added to the plates. After incubation at 4° C. for 1 hour, plates were washed 3 times with PBST. Then, a RPE coupled goat anti-Human IgG secondary antibody (Thermo Cat #: PAI-86078) diluted 500× was added to the plates. After incubation at 4° C. for 1 hour, plates were washed with PBS for 3 times and then the cell fluorescence was monitored using a FACS machine (BD). Based on the binding affinity and specificity, 4 clones, 18F2-5, 18F2-30, 18F2-35 and 18F2-66, which showed higher binding affinity than the parent clone 18F2, were selected for further investigation. The $EC_{50}$ of the 4 selected chimeric monoclonal antibodies were shown in Table 2, with an $EC_{50}$ comparable to IMAB362, a reference anti-Claudin 18.2 antibody synthesized using the amino acids sequences disclosed in patent application WO2014/146672 A1.

TABLE 2

Binding affinity $EC_{50}$ of Anti-Claudin 18.2 antibodies

| | FACS($EC_{50}$: M) | |
|---|---|---|
| Clone | HEK-293A/h Claudin18.2 | HEK-293A/hClaudin18.1 |
| IMAB362 | 6.34E−10 | N/A |
| 18F2 | 1.26E−9 | N/A |
| 18F2-30 | 5.62E−10 | N/A |
| 18F2-35 | 5.09E−10 | N/A |
| 18F2-66 | 5.24E−10 | N/A |
| 18F2-5 | 6.16E−10 | N/A |

Example 5 ADCC Activity of Anti-Claudin 18.2 Antibodies

Figure 2:
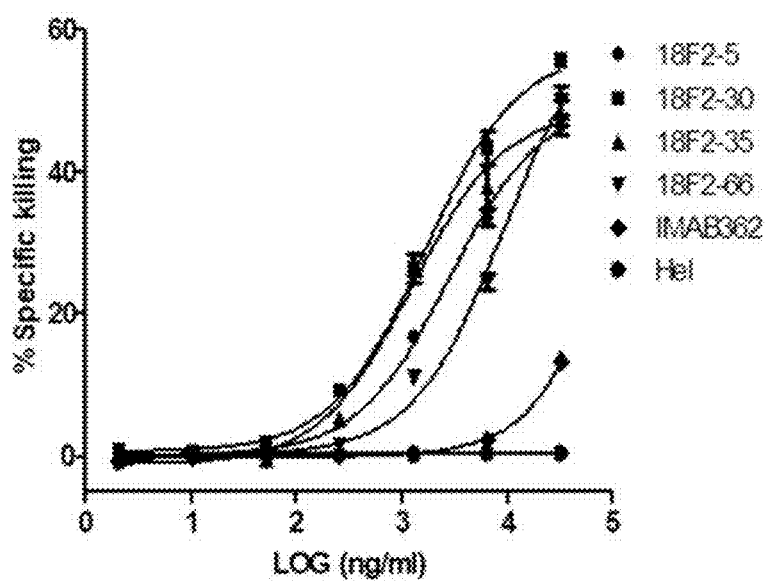
FIG. 2 shows ADCC activity of anti-Claudin 18.2 antibodies against MC38 cells overexpressing human Claudin 18.2.

Purified antibodies were analyzed for their capability to induce antibody-dependent cellular cytotoxicity (ADCC) activity against MC38 cells (Cober, China) stably overexpressing human Claudin 18.2 (MC38/hClaudin 18.2). Briefly, MC38/hClaudin 18.2 cells were generated by lentivirus transfection system as described in Example 1. Then MC38/hClaudin 18.2 cells and effector cell NK92MI-CD16a (Huabo Bio) were centrifuged at 1200 rpm for 5 minutes. These cells were then suspended with the ADCC assay culture medium (MEM medium, Gibco, Cat #: 12561-056; 1% FBS, EX-cell, Cat #: FND500; 1% BSA, VETEC, Cat #:V900933-1KG), and the cell viability was ~90% according to cell counting. MC38/hClaudin 18.2 cell density was adjusted to $4 \times 10^5$/ml, and NK92MI-CD16a cell density was adjusted to $2 \times 10^6$/ml. Then 50 µl of MC38/hClaudin 18.2 cells and 50 µl of NK92MI-CD16a cells (effector-target ratio was 5:1) were added to each well of a 96-well plate. Antibodies diluted to different concentrations were separately added to each well to a final concentration of 32000 ng/ml, 6400 ng/ml, 1280 ng/ml, 256 ng/ml, 51.2 ng/ml, 10.24 ng/ml, 2.048 ng/ml, respectively. The samples were incubated at 37° C. for 4 h, and then LDH developing solution (Cytotoxicity Detection Kit PLUS (LDH), Roche, Cat #: 04744926001) was added at a concentration of 100 µl/well. The mixture were incubated in dark at room temperature for 20 minutes and then the plates were read using a MD SpectraMax i3. An anti-HEL isotype control antibody (LifeTein, LLC, Cat. #: LT12031) was used a negative control and IMAB362 was used as a reference anti-Claudin 18.2 antibody. As shown in FIG. 2, the four selected chimeric antibodies, 18F2-5, 18F2-30, 18F2-35 and 18F2-66, were able to induce killing of MC38/hClaudin 18.2 cells by NK92MI-CD16a.

Figure 3A:
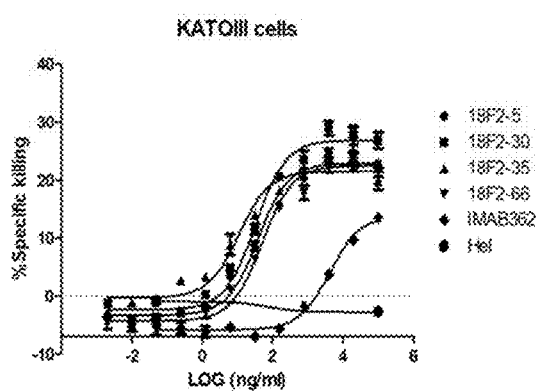
FIGS. 3A and 3B show ADCC activity of anti-Claudin 18.2 antibodies against EOF pretreated KATOIII cells (A) or NUGC4 cells (B).
Figure 3B:
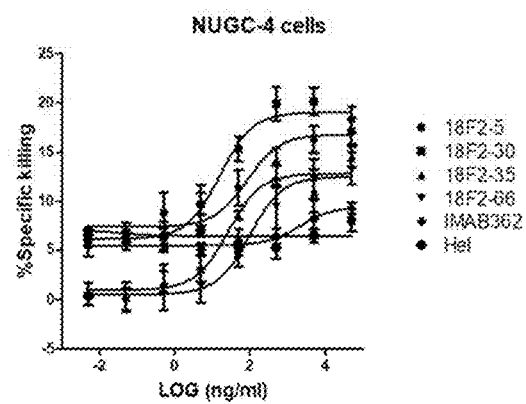

The anti-Claudin 18.2 antibodies were further tested for their ADCC activity against KATO-III (Cobioer, China), and NUGC-4 cells (Cobioer, China), both of which were reported to have high endogenous expression of human Claudin 18.2. Briefly, the target cells were pretreated with 10 ng/ml epitubicin (Apexbio, Cat #. A2451-100 mg), 500 ng/ml oxaliplatin (Ark pharm, Cat #. Ak-72813) and 10 ng/ml 5-FU (Acros, Cat #. Un12811) (EOF) for 72 hours, and then the drugs were removed and the cells were cultured in normal culture medium (DMEM+10% FBS) for another 24 hours. The ADCC assay was performed using the protocol as mentioned above using KATO-III or NUGC-4 cells as the target cells. $2 \times 10^5$ NK92MI-CD16a cells and $2 \times 10^4$ KATO-III cells or NUGC-4 cells (effector-target ratio was 10:1) were used in each assay. As shown in FIGS. 3A and 3B, the four monoclonal antibodies 18F2-5, 18F2-30, 18F2-35 and 18F2-66, were able to induce killing of KATO-III or NUGC-4 cells by NK92MI-CD16a cells.

Figure 4A:
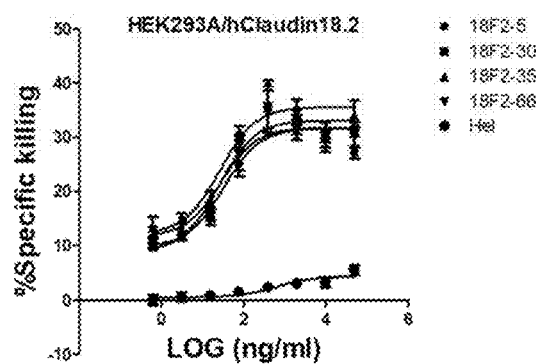
FIGS. 4A and 4B shows ADCC activity of anti-Claudin 18.2 antibodies against HEK293A cells overexpressing human Claudin 18.2 (A) or human Claudin 18.1 (B).
Figure 4B:
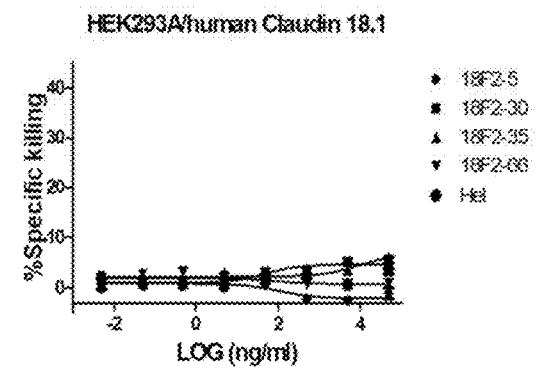

To further confirm whether anti-Claudin 18.2 antibodies specifically induce the ADCC activity on Claudin 18.2 positive cells, these antibodies were tested for their capacities of inducing ADCC activity against HEK293A cells overexpressing human Claudin 18.2 or Claudin 18.1. Briefly, $1\times10^5$ NK92MI-CD16a cells and $2\times10^4$ HEK293A cells overexpressing human Claudin 18.1 or 18.2 (effector-target ratio was 5:1) were used in each assay. As shown in FIGS. 4A and 4B, the 4 tested antibodies 18F2-5, 18F2-66, 18F2-30, and 18F2-35, specifically induced ADCC activity against HEK293A cells expressing human Claudin 18.2 while no cytotoxicity effect was observed on HEK293A cells overexpressing human Claudin 18.1.

Example 6 CDC Activity of Anti-Claudin 18.2 Antibodies

Figure 5:
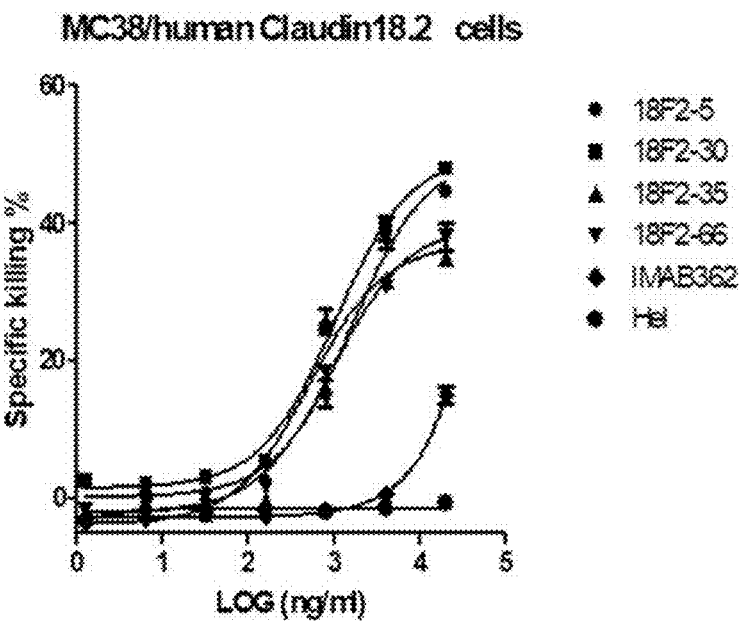
FIG. 5 shows CDC activity of anti-Claudin 18.2 antibodies against MC38 cells overexpressing human Claudin 18.2.

The capability of the anti-Claudin 18.2 antibodies to induce CDC activity against MC38 cells stably overexpressing human Claudin 18.2 (MC38/hClaudin 18.2, generated in Example 5) was measured using the Cytotoxicity Detection Kit (Roche, Cat #: 04744926001). Briefly, target cells MC38/human Claudin 18.2 cells were centrifuged at 1200 rpm for 4 minutes, and then the cells were suspended in DMEM medium with 1% FBS. Cell density of MC38/hClaudin 18.2 cells was adjusted to $3\times10^5$ cells/ml, and 100 μl of cells was added to each well of 96-well plates. Antibodies diluted to various concentrations were separately added, and their final concentrations were 20 μg/ml, 4 μg/ml, 0.8 μg/ml, 0.16 μg/ml, 0.032 μg/ml, 0.0064 μg/ml and 0.00128 μg/ml, respectively. Normal human serum complement (Quidel, Cat #: A113) was added at a final concentration of 5%, and then the obtained mixture was incubated at 37° C. for 2 h. LDH developing solution was added at a concentration of 100 μl/well, and then the samples were incubated in dark at room temperature for 20 minutes. An MD SpectraMax i3 instrument was used to read the plates. Anti-Claudin 18.2 antibody IMAB362 was used as a reference and an anti-HEL monoclonal antibody was used as a negative control. As shown in FIG. 5, all test antibodies, 18F2-5, 18F2-30, 18F2-35 and 18F2-66, exhibited a strong CDC activity in a dose dependent manner.

Example 7 Binding Stability of Anti-Claudin 18.2 Antibodies to Human Claudin 18.2

The purified anti-Claudin 18.2 antibodies were further analyzed for their binding stability to HEK293A/hClaudin 18.2 cells by FACS. Briefly, $10^5$ HEK293A/hClaudin 18.2 cells were seeded into each well of 96-well plates and 10 μg/ml anti-Claudin 18.2 antibodies were added to the plates. After incubation at 4° C. for 1 hour, plates were washed 3 times with PBST, and cells were suspended with cell culture medium (DMEM). Cells were further incubated at 37° C. for 0 h, 3 h or 5 h respectively. Then, a RPE coupled goat anti-Human IgG secondary antibody (Thermo, Cat #: PAI-86078) diluted at 500× was added to the plates. After incubation at 4° C. for 1 hour, plates were washed with PBS for 3 times and then the cell fluorescence was monitored using a FACS machine (BD).

Figure 6:
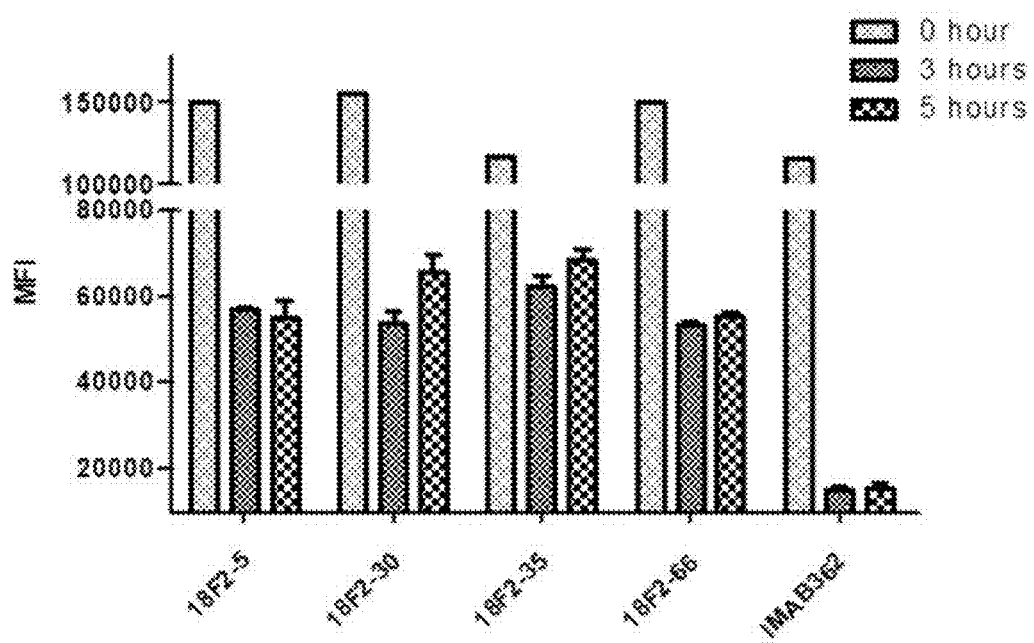
FIG. 6 shows binding stability of anti-Claudin 18.2 antibodies to HEK293A cells overexpressing human Claudin 18.2 in FACS assay, where HEK293A cells were incubated with anti-Claudin 18.2 antibodies at 4° C. for 1 hour, and incubated at 37° C. for another 0 hour, 3 hour or 5 hour after unbound antibodies were removed.

As shown in FIG. 6, all 4 antibodies (18F2-5, 18F2-30, 18F2-35 and 18F2-66) displayed higher binding stability than IMAB362 in the assay, which seemed to be consistent with their higher ADCC and CDC activity, suggesting that the higher binding stability may contribute to higher ADCC and CDC activity.

Example 8 Humanization of Anti-Claudin 18.2 Antibodies

Anti-Claudin 18.2 antibodies, 18F2-5, 8F2-30, 18F2-35 and 18F2-66, were selected for humanization and further investigation. Humanization of the murine antibodies was conducted using the well-established CDR-grafting method as described in detail below.

To screen acceptor frameworks for humanization of chimeric antibodies 18F2-5, 18F2-30, 18F2-35 and 18F2-66, the light and heavy chain variable chain sequences of above antibodies were blasted against the human immunoglobulin gene database in NCBI website (http://www.ncbi.nlm.nih.gov/igblast/) to identify the most homologous human germline IGVH and IGVKas the acceptor for humanizations, respectively. For the above 4 antibodies, the human heavy chain acceptor selected was IGHV1-46*01, and the human light chain acceptor selected was IGKV4-1*01.

Three dimensional structures were simulated for the variable domains of above 4 antibodies in order to identify key framework residues that might play important roles in supporting CDR loop structures, thus designing back mutations in the humanized antibodies. Selected structure templates had the same classes of canonical loop structures in L-CDR1, L-CDR2, L-CDR3, H-CDR1, H-CDR2 and H-CDR3 to 18F2-5, 8F2-30, 18F2-35 and 18F2-66, respectively. Using the structural templates selected, structural models were built by replacing the murine frameworks with human acceptor's frameworks for heavy and light chains. Three-dimensional structural modeling simulation was then performed to identify key framework residues that might be important in supporting the CDR-loop structures or the heavy and light chain interface. When both the murine antibody and the human acceptor framework share the same residue at a certain site in the framework, the human germline residue was kept. On the other hand, when the murine antibody and human germline acceptor framework have different residues at a certain site in the framework, the importance of this residue was evaluated by structural modeling. If a residue in the murine antibody's framework was found to interact with and influence the CDR residues, then this residue was back-mutated to murine residue. Table 3 below listed structural templates used in antibody structure simulation.

TABLE 3

Structural templates used in antibody structure simulations

| Antibody chain | PDB code of template structure | Sequence identity | Sequence similarity |
|---|---|---|---|
| 18F2-30 Heavy chain | 1WT5 | 81% | 88% |
| 18F2-30 Light chain | 4LEO | 93% | 98% |
| 18F2-35 Heavy chain | 1WT5 | 81% | 88% |
| 18F2-35 Light chain | 4LEO | 94% | 97% |
| 18F2-5 Heavy chain | 1WT5 | 81% | 87% |
| 18F2-5 Light chain | 4LEO | 92% | 97% |
| 18F2-66 Heavy chain | 3SQO | 83% | 88% |
| 18F2-66 Light chain | 4LEO | 93% | 98% |

Based on the structural modeling as described above, 11 potential back-mutations (R38K, A40R, M48I, R67K, M70L, R72V, T74K, T76S, V79A, R87T, A97T) were identified for heavy chain of the anti-Claudin 18.2 antibodies and 6 potential back-mutations (D9S, A12T, R18K, N22S, V89L, Q106S) were identified for the light chain.

As summarized in Table 4 below, for each affinity-maturated anti-Claudin 18.2 antibody, 7 humanized heavy chain variable regions and 3 humanized light chain variable regions were designed.

TABLE 4

Back-mutations designed for anti-Claudin 18.2 antibodies

| Heavy chain variable region | Heavy chain back-mutations | Light chain variable region | Light chain back-mutations |
|---|---|---|---|
| VH0 | None | VL0 | None |
| VH2 | M48I, M70L, R72V, T74K | VL2 | D9S, A12T, R18K, V89L |
| VH3 | M48I, M70L, R72V | VL3 | D9S, A12T, R18K, N22S, V89L, Q106S |
| VH4 | A40R, M48I, M70L, R72V, T74K | | |
| VH5 | A40R, M48I, M70L, R72V, T74K, V79A, A97T | | |
| VH6 | A40R, M48I, M70L, R72V, T74K, T76S, V79A, R87T, A97T | | |
| VH7 | A40R, R38K, M48I, R67K, M70L, R72V, T74K, V79A, A97T | | |

DNA sequences encoding the humanized full length antibodies (respective heavy/light chain variable region (summarized in table 1) plus the human IgG1/kappa constant regions ((SEQ ID Nos.: 67 and 68))) were chemically synthesized and then subcloned into the expression vector pCDNA3 (Invitrogen) using the EcoR I and Xho I, Cla I and Hind III restriction sites, respectively. All expression constructs were confirmed by DNA sequencing. The 42 humanized Claudin 18.2 antibodies (10 for 18F2-5, 11 for 18F2-30, 11 for 18F2-35 and 10 for 18F2-66) were transiently expressed and purified using the protocols as described in Example 3. The purified humanized antibodies were then further characterized as described in detail below.

Example 9 Humanized Anti-Claudin 18.2 Antibodies Bound to Human Claudin 18.2 Expressed on HEK293A Cells The 42 humanized anti-Claudin 18.2 antibodies were further tested for the ability to bind to human Claudin 18.2 or human Claudin 18.1 expressed on HEK293A/hClaudin 18.2 cells or HEK293A/hClaudin 18.1 cells, respectively. FACS was done as described in Example 4.

Figure 7A:
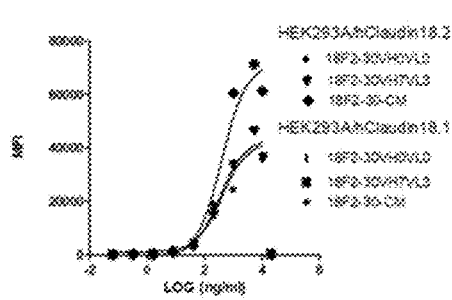
FIGS. 7A, 7B and 7C show binding affinity of humanized anti-Claudin 18.2 antibodies to HEK293A cells overexpressing human Claudin 18.2 or human Claudin 18.1 in FACS assay, where the humanized anti-Claudin 18.2 antibodies includes 18F2-30VH0VL0, 18F2-30VH7VL3 and 18F2-30 (A), 18F2-35VH0VL0, 18F2-35VH7VL3 and 18F2-35 (B), and 18F2-5VH0VL0, 18F2-5VH7VL3 and 18F2-5 (C).
Figure 7B:
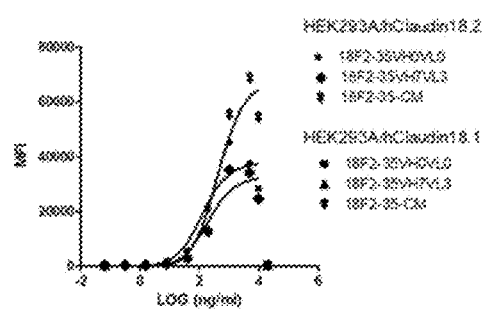
Figure 7C:
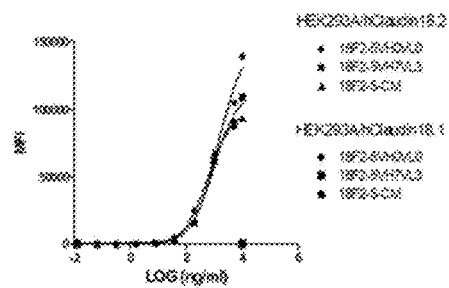

The binding affinity of the representative humanized anti-Claudin 18.2 antibodies were shown in FIG. 7A-7C. The binding affinities of all the humanized antibodies were similar to their parent antibodies, and none of them had binding affinity to human Claudin 18.1, indicating their high and specific binding to human Claudin 18.2. Based on the binding affinity, 6 of them (18F2-5VH0VL0, 18F2-5VH7VL3, 18F2-30VH0VL0, 18F2-30VH7VL3, 18F2-35VH0VL0, 18F2-35VH7VL3) were selected for further investigation.

Example 10 CDC Activity of Humanized Anti-Claudin 18.2 Antibodies

The humanized antibodies were further assayed for their ability of inducing CDC activity against human Claudin 18.2-overexpressing MC38 cells. CDC assay was performed according to the protocol described in Example 6. Anti-Claudin 18.2 antibody IMAB362 was used as a reference antibody and an anti-HEL monoclonal antibody was used as a negative control.

Figure 8A:
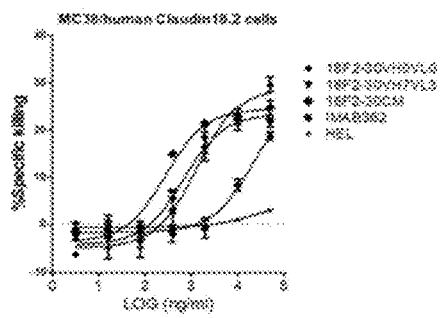
FIGS. 8A, 8B and 8C show CDC activity of humanized anti-Claudin 18.2 antibodies against MC38 cells overexpressing human Claudin 18.2, where the humanized anti-Claudin 18.2 antibodies were 18F2-30VH0VL0, 18F2-30VH7VL3 and 18F2-30 (A), 18F2-35VH0VL0, 18F2-35VH7VL3 and 18F2-35 (B), and 18F2-5VH0VL0, 18F2-5VH7VL3 and 18F2-5 (C).
Figure 8B:
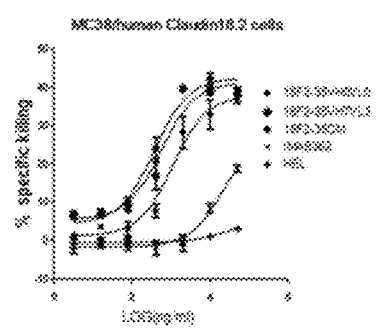
Figure 8C:
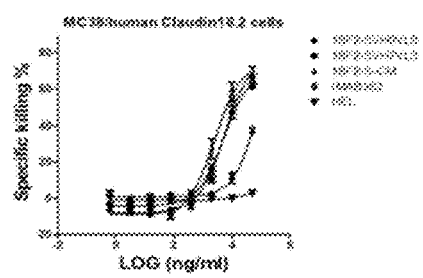

The result of CDC assay was shown in FIG. 8A-8C, which indicated that all the tested humanized anti-Claudin 18.2 antibodies displayed strong CDC activity.

Example 11 ADCC Activity of Humanized Anti-Claudin 18.2 Antibodies

The capability of humanized antibodies to induce ADCC effect was assayed by using NK92MI-CD16a cells as the effector cells. ADCC assay was done according to the protocol in Example 5.

Figure 9A:
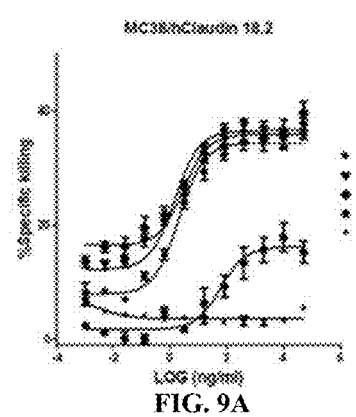
FIGS. 9A, 9B and 9C show ADCC activity of humanized anti-Claudin 18.2 antibodies against MC38 cells overexpressing human Claudin 18.2, where the humanized anti-Claudin 18.2 antibodies were 18F2-30VH0VL0, 18F2-30VH7VL3 and 18F2-30 (A), 18F2-35VH0VL0, 18F2-35VH7VL3 and 18F2-35 (B), and 18F2-5VH0VL0, 18F2-5VH7VL3 and 18F2-5 (C).
Figure 9B:
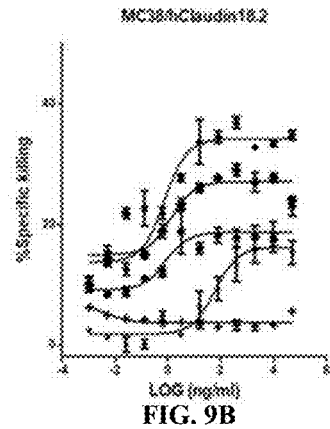
Figure 9C:
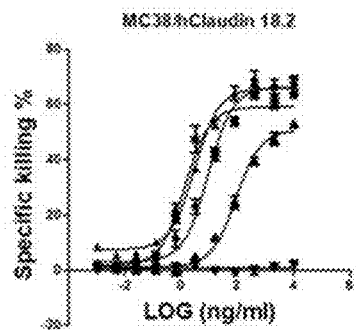

Firstly, the humanized anti-Claudin 18.2 antibodies were analyzed for their capability to induce ADCC against MC38/hClaudin 18.2 cells. As shown in FIG. 9A-9C, humanized antibody 18F2-35VH0VL0 and 18F2-30VH7VL3 displayed stronger effect in ADCC assay among all the humanized antibodies.

Based on this result, the ADCC effect of these humanized anti-Claudin 18.2 antibodies against EOF pretreated KATO-III cells and NUGC-4 cells were further tested, both of which were known to have high endogenous expression of Claudin 18.2 protein. The KATO-III cells and NUGC-4 cells were pretreated with 10 ng/ml epitubicin (Apexbio, Cat. A2451-100 mg), 500 ng/ml oxaliplatin (Ark pharm, Cat. Ak-72813) and 10 ng/ml 5-FU (Acros, Cat. Un12811) (EOF) for 72 hours, and then the drugs were removed and the cells were cultured in normal culture medium (DMEM+10% FBS) for another 24 hours. The ADCC assay was performed using the protocol as mentioned in Example 5.

Figure 10A:
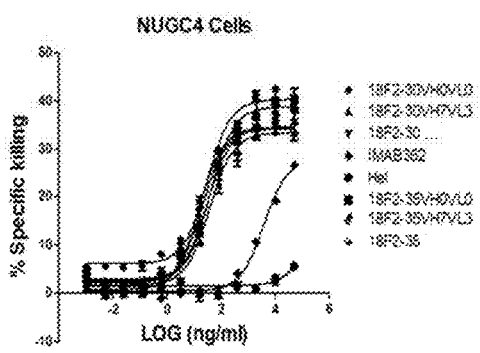
FIGS. 10A and 10B show ADCC activity of humanized anti-Claudin 18.2 antibodies against EOF pretreated NUGC4 (A) or KATOIII cells (B).
Figure 10B:
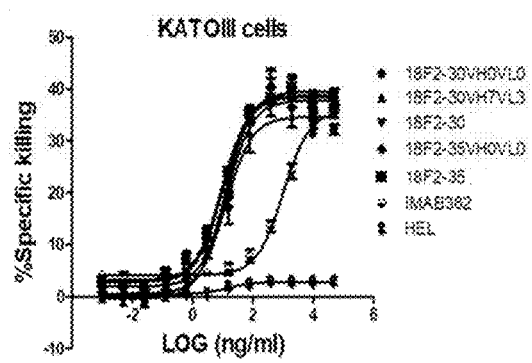

As shown in FIGS. 10A and 10B, all the 6 tested humanized anti-Claudin 18.2 antibodies displayed strong ADCC activity on the target cells KATO-III or NUGC-4 cells as compared to reference antibody IMAB362.

Example 12 Specificity of ADCC and CDC Activity of Humanized Anti-Claudin 18.2 Antibodies In order to confirm that anti-Claudin 18.2 antibodies displayed ADCC or CDC activities specifically on target cells expressing Claudin 18.2 but not on cells expressing Claudin 18.1, ADCC and CDC assays were performed using HEK293A cells expressing human Claudin 18.1 (HEK293A/hClaudin 18.1 cells) or human Claudin 18.2 (HEK293A/hClaudin 18.2 cells) as the target cells, following the protocols described in Example 5 and 6. As shown in FIG. 11A, 11B (ADCC assay) and FIG. 12A, 12B (CDC assay), all the tested anti-Claudin 18.2 antibodies induced ADCC and CDC activity only on HEK293A cells expressing human Claudin 18.2 but not on cells expressing human Claudin 18.1, suggesting that the ADCC and CDC activity induced by anti-Claudin 18.2 antibodies were highly specific to cells expressing human Claudin 18.2.

Example 13 Binding Stability of Humanized Anti-Claudin 18.2 Antibodies to Human Claudin 18.2

Ten humanized anti-Claudin 18.2 antibodies were chosen to analyze their binding stability with HEK293A cells stably overexpressing human Claudin 18.2 (HEK293A/hClaudin 18.2) by FACS, according to the protol described in Example 7. Anti-Claudin 18.2 antibody IMAB362 was used as a reference and an anti-HEL monoclonal antibody was used as a negative control.

Figure 13:
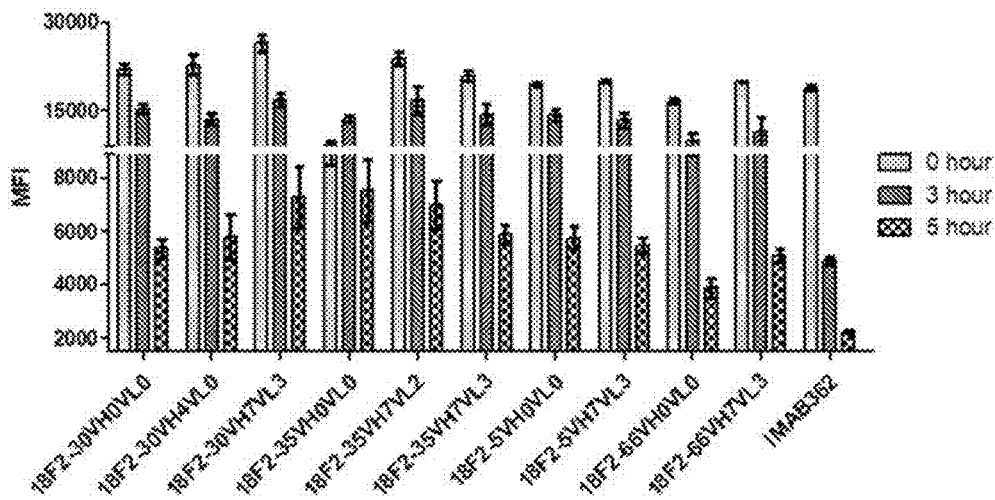
FIG. 13 shows binding stability of humanized anti-Claudin 18.2 antibodies to HEK293A cells overexpressing human Claudin 18.2 assayed, where HEK293A cells were incubated with humanized anti-Claudin 18.2 antibodies at 4° C. for 1 hour, and incubated at 37° C. for another 0 hour, 3 hour or 5 hour after unbound antibodies were removed.
Figure 14:
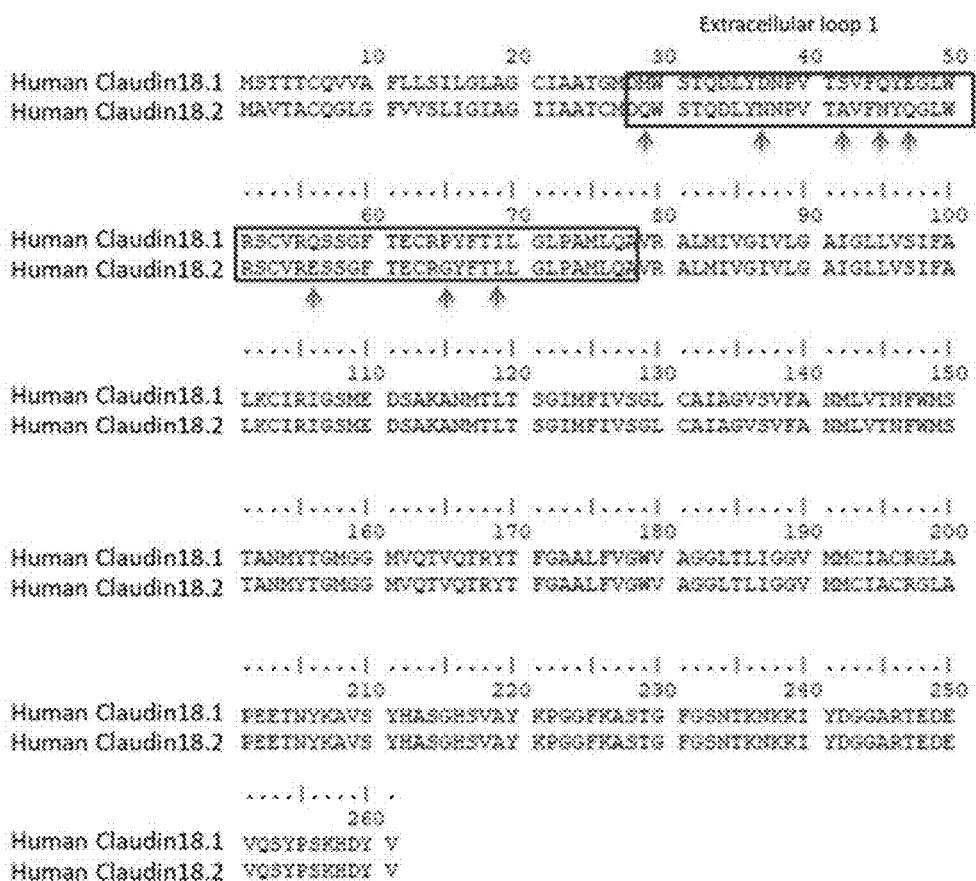
FIG. 14 shows amino acid sequence alignment of human Claudin 18.1 to human Claudin 18.2, where the boxes indicats the extracellular loop 1 region, and the arrows indicats amino acid difference in this region.

As shown in FIG. 13, the humanized antibodies had different binding stabilities, and the binding stability tended to consistent with the ADCC and CDC test results.

Example 14 Epitope Mapping of Humanized Anti-Claudin 18.2 Antibodies

The binding epitope for each humanized anti-Claudin 18.2 antibody was investigated. Sixteen HEK293A cell lines expressing human Claudin 18.2 or Claudin 18.1 with various mutations in its extracellular loop 1 were generated, the amino acid sequences of human Claudin 18.2 or Claudin 18.1 mutants can be found in Table 5 below. In specific, 8 human Claudin 18.2 mutants were designed in which a single amino acid residue in the extracellular loop 1 was replaced with its counterpart in the extracellular loop 1 of Claudin 18.1. HEK-293A cell lines stably overexpressing these Claudin 18.2 or Claudin 18.1 mutants were generated by lentivirus infection following the protocol in Example 1. And then FACS was performed to study the binding affinity of the anti-Claudin 18.2 antibodies to each of the mutants.

As shown in Table 5, all the anti-Claudin 18.2 antibodies, including IMAB362, had no binding to Mutant 6-expressing cells which beared E56Q mutation, suggesting that E56 was an essential amino acid residue for antibody-Claudin 18.2 interaction. In addition, data showed that Claudin 18.2 with A42S (mutant 3) or N45Q (mutant 4) mutation totally lost binding by IMAB362 and lost partial binding by humanized anti-Claudin 18.2 antibody 18F2-30VH0VL0, 18F2-30 VH7VL3 or 18F2-35VH0VL0. Taken together, these data suggested that the antibodies 18F2-30VH0VL0, 18F2-30VH7VL3 and 18F2-35VH0VL0 bound to a different epitope in the extracellular loop 1 of human Claudin 18.2, as compared to IMAB362.

Based on the above results, another five mutants were designed with double or multi-sites mutations. As shown in Table 5, IMAB362 displayed no binding to all 5 mutants while all the humanized antibodies displayed either full or partial binding affinity to mutants 9, 10 and 11, confirming that A42 and N45 of human Claudin 18.2 were essential amino acid residues for IMAB362 binding affinity but not for 18F2-30VH0VL0, 18F2-30VH7VL3 or 18F2-35VH0VL0.

Figure 15:
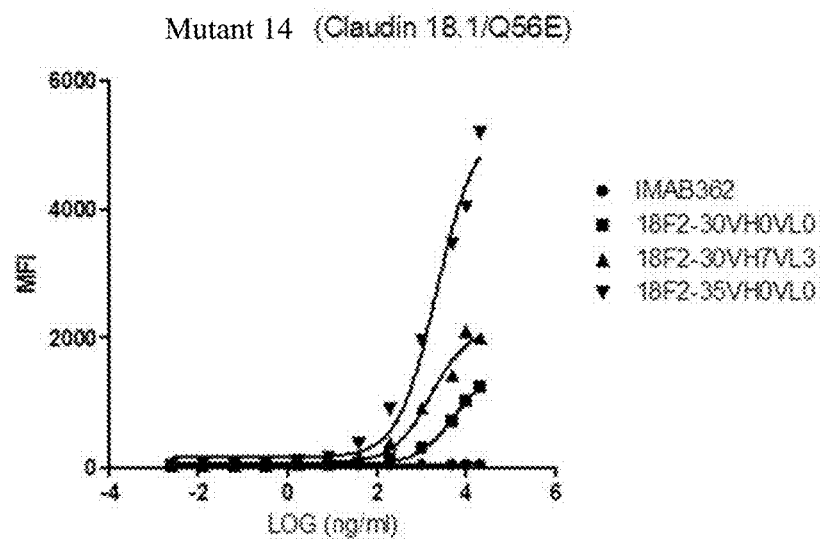
FIG. 15 shows binding affinity of anti-Claudin 18.2 antibodies against HEK293A cells overexpressing mutant 14.
Figure 16A:
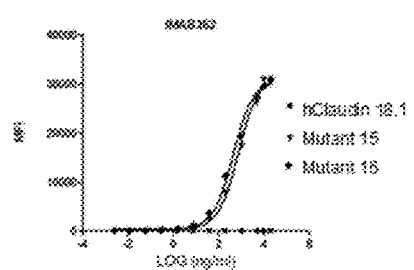
FIG. 16A-16D show binding affinity of anti-Claudin 18.2 antibodies against HEK293A cells overexpressing human Claudin 18.1, mutant 15 (Claudin 18.1/S42A/Q45N/Q56E) or mutant 16 (Claudin 18.1/S42A/Q45N E47Q/Q56E), where the antibodies were IMAB362(A), 18F2-35VH0VL0 (B), 18F2-30VH7VL3 (C) and 18F2-30VH0VL0 (D).
Figure 16B:
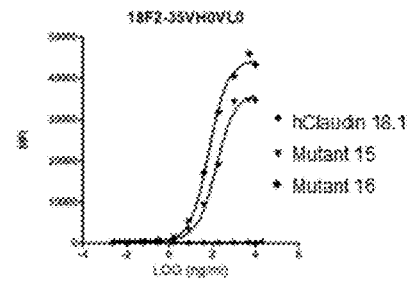
Figure 16C:
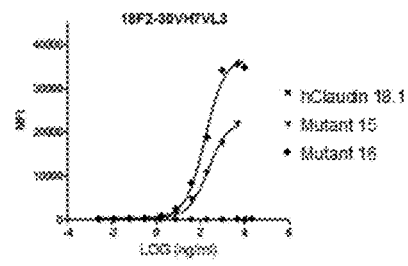
Figure 16D:
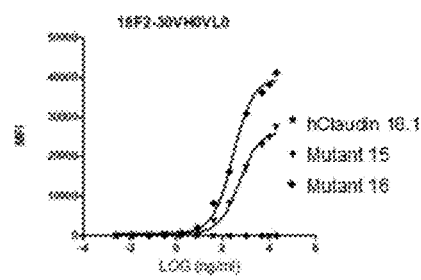

In order to further confirm this conclusion, another three cell lines overexpressing human Claudin 18.1 mutants were generated. Consistent with above results, all the antibodies except IMAB362 can bind to mutant 14-expressing cells, indicating different binding patterns between the humanized antibodies of the invention and IMAB362 (see FIG. 15). Further, it can be seen from FIG. 16A-16D that E47Q back mutation did not improve Claudin 18.2 binding affinity of IMAB362, but enhanced the binding affinity of 18F2-30VH0VL0, 18F2-30VH7VL3 and 18F2-35VH0VL0, suggesting that human Claudin 18.2/Q47 is an important amino acid residue for Claudin 18.2 binding affinity of 18F2-30VH0VL0, 18F2-30VH7VL3 and 18F2-35VH0VL0, but not for IMAB362.

In summary, we conclude that the humanized anti-Claudin 18.2 antibodies 18F2-30VH0VL0, 18F2-30VH7VL3 and 18F2-35VH0VL0 bound to quite different epitopes in the extracellular loops 1 of human Claudin 18.2 as compared to the reference antibody IMAB362.

TABLE 5

Amino acid SEQ ID NOs. of human Claudin 18.1 and human Claudin 18.2 mutants and Antibodies' binding capacity to mutants

| Protein | Mutant No. | Amino acid residue mutation | SEQ ID NO. | Antibody's binding capacity to WT/mutant Claudin 18.1/18.2 | | | |
|---|---|---|---|---|---|---|---|
| | | | | IMAB362 | 18F2-30VH0VL0 | 18F2-30VH7VL3 | 18F2-35VH0VL0 |
| Claudin 18.2 | WT | / | 72 | +++ | +++ | +++ | +++ |
| | Mutant 1 | Q29M | 73 | ++ | ++ | ++ | ++ |
| | Mutant 2 | N37D | 74 | ++ | ++ | ++ | ++ |
| | Mutant 3 | A42S | 75 | — | ++ | ++ | ++ |
| | Mutant 4 | N45Q | 76 | — | ++ | ++ | ++ |
| | Mutant 5 | Q47E | 77 | ++ | ++ | ++ | ++ |
| | Mutant 6 | E56Q | 78 | — | — | — | — |
| | Mutant 7 | G65P | 79 | ++ | ++ | ++ | ++ |
| | Mutant 8 | L69I | 80 | ++ | ++ | ++ | ++ |
| | Mutant 9 | A42S/N45Q | 81 | — | + | + | + |
| | Mutant 10 | A42S/Q47E | 82 | — | ++ | ++ | + |
| | Mutant 11 | N45Q/Q47E | 83 | — | ++ | ++ | + |
| | Mutant 12 | A42S/N45Q/Q47E | 84 | — | + | + | — |
| | Mutant 13 | A42S/N45Q/Q47E/E56Q | 85 | — | — | — | — |
| Claudin 18.1 | WT | / | 70 | — | — | — | — |
| | Mutant 14 | Q56E | 86 | — | + | + | + |
| | Mutant 15 | S42A/Q45N/Q56E | 87 | ++ | ++ | ++ | ++ |
| | Mutant 16 | S42A/Q45N/E47Q/Q56E | 88 | ++ | ++ | ++ | ++ |

Example 15 ADCC Activity of Humanized Anti-Claudin 18.2 Antibodies by Human PBMCs or Vγ9Vδ2 T Cells Humanized anti-Claudin 18.2 antibodies were further analyzed for their capability to induce ADCC activity against MC38/hClaudin 18.2 cells (prepared in Example 5) or EOF pretreated NUGC-4 cells by human PBMC, wherein the MC38/hClaudin 18.2 cells were generated by infection of pLV-EGFP(2A)-Puro which expressed GFP proteins. Human PBMC were prepared by density gradient centrifugation using lymphocyte isolation solution, and cultured in medium (RIPM1640+10% FBS+300 IU IL-2) overnight.

The ADCC assays were carried out by using LIVE/DEAD Fixable Dead Cell Stains Kit (Thermo Fisher, USA, Cat #: L34964). Both target cells and effector cells (PBMC) were centrifuged at 1200 rpm for 5 minutes. The cells were then suspended in ADCC experimental culture medium (RIPM1640 medium+1% FBS), and the cell viability should be ~90% according to cell counting. The target cell density was adjusted to $4\times10^5$/ml, and PBMC cell density was adjusted to $8\times10^6$/ml. Then 50 μl of MC38/hClaudin 18.2 cells and 50 μl of PBMC (effector-target ratio was 20:1) were added in each well. Antibodies of different concentrations were separately added to achieve final concentrations. The antibody final concentrations for MC38/hClaudin 18.2 cells were 800 ng/ml, 32 ng/ml and 6.4 ng/ml, and concentrations for NUGC-4 cells were 4000 ng/ml, 160 ng/ml, 64 ng/ml and 2.5 ng/ml. Then the samples were incubated at 37° C. for 12 hours. The mixture were washed with PBS for 3 times, and then incubated with LIVE/DEAD Fixable Dead Cell Stains at 37° C. for 30 minutes. The cells were washed for 3 times with PBS, and then analysed by FACS. The apoptosis ratio of GFP positive cells (MC38/hClaudin 18.2 cells) was calculated.

For the assay against NUGC-4 cells, the NUGC-4 cells were pretreated with 10 ng/ml epitubicin (Apexbio, Cat. A2451-100 mg), 500 ng/ml oxaliplatin (Ark pharm, Cat. Ak-72813) and long/ml 5-FU (Acros, Cat. Un12811) (EOF) for 72 hours, and then the agents were removed. The cells were cultured in normal culture medium (DMEM+10% FBS) for another 24 hours. NUGC-4 cells were labeled with carboxyfluorescein succinimidyl ester (CFSE, Invitrogen, USA, Cat #: C34554) according to the manufacturer's instructions. ADCC assay was performed as described above, except that the ratio of ADCC effector cell to target cell was 50:1.

Previous studies had shown that Vγ9Vδ2T cells were important for the ADCC activity of anti-human Claudin 18.2 antibodies. Vγ9Vδ2 T cells were enriched in human PBMC in the present example. In particular, PBMCs were collected and cultured in Vγ9Vδ2 T cell-inducing DMEM medium with 10% FBS, 300 IU IL-2 and 1 μM zoledronic acid (ZA). After 14 days, cells were harvested and used as the effector cells in ADCC assay. With the assay using MC38/hClaudin 18.2 cells as target cells, the E/T ratio was 20:1; while when EOF pretreated NUGC-4 cells were used as target cells, the E/T ratio was 50:1. The detail ADCC protocol was just the same as description above.

As shown in FIG. 17A, 17B (PBMC as effector cells) and FIG. 18A, 18B (Vγ9Vδ2T cells as effector cells), all the antibodies can induce strong ADCC activity on the targeted cells by PBMC and Vγ9Vδ2T cells in a dose dependent manner. The ADCC activity by Vγ9Vδ2T cells was indeed stronger than that by PBMC, which was consistent with previous studies.

Example 16 In Vivo Anti-Tumor Effect of Anti-Claudin 18.2 Antibodies

Six anti-Claudin 18.2 antibodies (18F2-SVH0VL0, 18F2-5VH7VL3, 18F2-30VH0VL0, 18F2-30VH7VL3, 18F2-35VH0VL0, and 18F2-35VH7VL3) were selected for in vivo anti-tumor activity study in C57 mice with murine colon adenocarcinoma cancer. In order to exhibit the ADCC activity of the antibodies in animal models, the variable region of the antibodies were fused with mouse IgG 2a/kappa constant regions to prepare full-length antibodies, the mIgG2a and kappa constant region amino acid sequences were set forth in SEQ ID NOs.: 89 and 90, respectively.

C57 mice were injected with $1\times10^6$ MC38 cells overexpressing human Claudin 18.2 (MC38/hClaudin 18.2) at the flank region at day 0. When tumors reached about 80 mm³, the animals were assigned to different groups (n=8) and i.p. administered with one of the antibodies at a dose of 10 mg/kg at Day 5, 7, 10, 12, 14, 17 and 19. Tumor growth was monitored over time, with volumes measured at Day 5, 7, 10, 12, 14, 17 and 19. Tumor measurements (width and length) were taken by caliper and tumor volume calculated by the formula TV=(length×width²)/2. The experiment was terminated before the tumor volume reached 3 cm³.

As shown in FIGS. 19A and 19B, all the tested antibodies inhibited tumor growth, with the antibody having 18F2-30VH0VL0 variable regions displaying the best anti-tumor effect.

Example 17 Anti-Tumor Effect of Anti-Claudin 18.2 Antibodies in Combination with Chemotherapy C57 mice were subcutaneously injected with $1\times10^6$ MC38 cells overexpressing human Claudin 18.2 (MC38/hClaudin 18.2) at the flank region at Day 0. When tumors reached about 80 mm³, the animals were assigned to different groups (n=10) and intraperitoneally administered with EOF (epitubicin (1.25 mg/kg), oxaliplatin (3.25 mg/kg) and 5-FU (56.25 mg/kg)) or control vehicle on Day 5 and 12, wherein the control group did not received EOF pretreatment. Then, on Day 6, 8, 11, 13, 15 and 18, these mice were intraperitoneally injected with 18F2-30-VH0VL0, 18F2-5-VH0VL0, 18F2-35-VH7VL3 (all three having mouse IgG 2a/kappa constant region, the mIgG2a and kappa constant region amino acid sequences were set forth in SEQ ID NOs.: 89 and 90, respectively.) or a control agent, at a dose of 10 mg/kg. Tumor growth was monitored over time, with volumes measured at Day 5, 7, 10, 12, 14, 17 and 19. Tumor measurements (width and length) were taken by caliper and tumor volume calculated by the formula TV=(length×width²)/2. The experiment was terminated before the tumor volume reached 3 cm³.

As shown in FIG. 20, all the tested antibodies showed synergistic anti-tumor effect with chemotherapic agents, among which the antibody having 18F2-30VH0VL0 variable regions displayed the best synergistic anti-tumor effect.

Example 18 ADCC and CDC Activity of Afucosylated Anti-Claudin 18.2 Antibodies SLC35c1-knockout CHOK1-AF cells was generated by Mabworks just as described in US2018/0022820 A1, and proteins expressed by this cell lines nearly did not have fucosylation modification.

Expression vectors were constructed by cloning respective heavy/light chain variable region for 18F2-30VH0VL0 and 18F2-35VH7VL3 plus the human IgG1/kappa constant regions (SEQ ID Nos.: 67 and 68) into appropriate restriction sites of pCDNA3.1 (Invitrogen, Carlsbad, USA), which were than transformed into the SLC35c1-knockout CHOK1-AF cells. Two kinds of afucosylated anti-Claudin 18.2 antibodies, called as 18F2-30VH0VL0AF and 18F2-35VH7VL3AF, were transiently expressed in the SLC35c1-knockout CHOK1-AF cells and then purified according to the protocol in Example 3.

The ADCC activity of the two afucosylated anti-Claudin 18.2 antibodies was assayed by using NK92MI-CD16a cells as the effector cells and EOF pretreated NUGC-4 cells as target cells. ADCC assay was done according to the protocol in Example 5.

The afucosylated antibodies were further assayed for their ability of inducing CDC activity against human Claudin 18.2-overexpressing MC38 cells. CDC assay was performed according to the protocol described in Example 6. Anti-Claudin 18.2 antibody IMAB362 was used as a reference antibody and an anti-HEL monoclonal antibody was used as a negative control.

As shown in FIGS. 21A and 21B, both 18F2-30VH0VL0AF and 18F2-35VH7VL3AF had higher ADCC activity than their respective parent antibody. Resutles in FIGS. 22A and 22B suggested that CDC activity of these two antibodies were not different from the parent antibodies.

While the invention has been described above in connection with one or more embodiments, it should be understood that the invention is not limited to those embodiments, and the description is intended to cover all alternatives, modifications, and equivalents, as may be included within the spirit and scope of the appended claims. All references cited herein are further incorporated by reference in their entirety.

We claim:

1. An isolated monoclonal antibody, or an antigen-binding portion thereof, binding to Claudin 18.2, comprising:

(1) a heavy chain variable region comprising a CDR1, a CDR2, and a CDR3 comprising the amino acid sequences of SEQ ID NOs: 1, 4, and 7, respectively; and a light chain variable region comprising a CDR1, a CDR2, and a CDR3 comprising the amino acid sequences of SEQ ID NOs: 10, 13 and 16, respectively;

(2) a heavy chain variable region comprising a CDR1, a CDR2, and a CDR3 comprising the amino acid sequences of SEQ ID NOs: 2, 4, and 8, respectively; and a light chain variable region comprising a CDR1, a CDR2, and a CDR3 comprising the amino acid sequences of SEQ ID NOs: 11, 13 and 16, respectively;

(3) a heavy chain variable region comprising a CDR1, a CDR2, and a CDR3 comprising the amino acid sequences of SEQ ID NOs: 2, 4, and 9, respectively; and a light chain variable region comprising a CDR1, a CDR2, and a CDR3 comprising the amino acid sequences of SEQ ID NOs: 10, 14 and 16, respectively;

(4) a heavy chain variable region comprising a CDR1, a CDR2, and a CDR3 comprising the amino acid sequences of SEQ ID NOs: 2, 5, and 9, respectively; and a light chain variable region comprising a CDR1, a CDR2, and a CDR3 comprising the amino acid sequences of SEQ ID NOs: 12, 13 and 16, respectively; or (5) a heavy chain variable region comprising a CDR1, a CDR2, and a CDR3 comprising the amino acid sequences of SEQ ID NOs: 3, 6, and 8, respectively; and a light chain variable region comprising a CDR1, a CDR2, and a CDR3 comprising the amino acid sequences of SEQ ID NOs: 10, 15 and 16, respectively.

2. The antibody, or the antigen-binding portion thereof, of claim 1, wherein the heavy chain variable region comprises an amino acid sequence set forth in SEQ ID NOs: 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49.

3. The antibody, or the antigen-binding portion thereof, of claim 1, comprising a light chain variable region comprising an amino acid sequence set forth in SEQ ID NO: 50, 51, 52, 53, 54, 55, 56, 57, 58, 59, 60, 61, 62, 63, 64, 65 or 66.

4. The isolated monoclonal antibody, or an antigen-binding portion thereof, of claim 1, comprising a heavy chain variable region and a light chain variable region, wherein the heavy chain and the light chain variable regions comprise amino acid sequences set forth in (1) SEQ ID NOs: 17 and 50, respectively; (2) SEQ ID NOs: 18 and 51, respectively; (3) SEQ ID NOs: 19 and 52, respectively; (4) SEQ ID NOs: 20 and 53, respectively; (5) SEQ ID NOs: 21 and 54, respectively; (6) SEQ ID NOs: 22 and 55, respectively; (7) SEQ ID NOs: 23 and 55, respectively; (8) SEQ ID NOs: 24 and 55, respectively; (9) SEQ ID NOs: 25 and 55, respectively; (10) SEQ ID NOs: 26 and 55, respectively; (11) SEQ ID NOs: 27 and 55, respectively; (12) SEQ ID NOs: 27 and 56, respectively; (13) SEQ ID NOs: 27 and 57, respectively; (14) SEQ ID NOs: 28 and 56, respectively; (15) SEQ ID NOs: 28 and 57, respectively; (16) SEQ ID NOs: 29 and 58, respectively; (17) SEQ ID NOs: 30 and 58, respectively; (18) SEQ ID NOs: 31 and 58, respectively; (19) SEQ ID NOs: 32 and 58, respectively; (20) SEQ ID NOs: 33 and 58, respectively; (21) SEQ ID NOs: 34 and 58, respectively; (22) SEQ ID NOs: 34 and 59, respectively; (23) SEQ ID NOs: 34 and 60, respectively; (24) SEQ ID NOs: 35 and 58, respectively; (25) SEQ ID NOs: 35 and 59, respectively; (26) SEQ ID NOs: 35 and 60, respectively; (27) SEQ ID NOs: 36 and 61, respectively; (28) SEQ ID NOs: 37 and 61, respectively; (29) SEQ ID NOs: 38 and 61, respectively; (30) SEQ ID NOs: 39 and 61, respectively; (31) SEQ ID NOs: 40 and 61, respectively; (32) SEQ ID NOs: 41 and 61, respectively; (33) SEQ ID NOs: 41 and 62, respectively; (34) SEQ ID NOs: 41 and 63, respectively; (35) SEQ ID NOs: 42 and 61, respectively; (36) SEQ ID NOs: 42 and 62, respectively; (37) SEQ ID NOs: 42 and 63, respectively; (38) SEQ ID NOs: 43 and 64, respectively; (39) SEQ ID NOs: 44 and 64, respectively; (40) SEQ ID NOs: 45 and 64, respectively; (41) SEQ ID NOs: 46 and 64, respectively; (42) SEQ ID NOs: 47 and 64, respectively; (43) SEQ ID Nos: 48 and 64, respectively; (44) SEQ ID NOs: 48 and 65, respectively; (45) SEQ ID NOs: 48 and 66, respectively; (46) SEQ ID NOs: 49 and 65, respectively; or (47) SEQ ID NOs: 49 and 66, respectively.

5. The isolated monoclonal antibody, or an antigen-binding portion thereof, of claim 1, comprising a heavy chain constant region having an amino acid sequence set forth in SEQ ID NOs: 67 or 89, or a light chain constant region having an amino acid sequence set forth in SEQ ID NOs: 68 or 90.

6. The antibody, or the antigen-binding portion thereof, of claim 1, which (a) binds human Claudin 18.2; (b) does not bind Claudin 18.1; (c) induces antibody dependent cell-mediated cytotoxicity against human Claudin 18.2-expressing cells; and (d) induces complement dependent cytotoxicity against human Claudin 18.2-expressing cells.

7. The antibody, or the antigen-binding portion thereof, of claim 1, which is an IgG1, IgG2 or IgG4 isotype.

8. The antibody, or the antigen-binding portion thereof, of claim 1, which is a mouse, human, chimeric or humanized antibody.

9. The antibody, or the antigen-binding portion thereof, of claim 1, which is an afucosylated antibody.

10. A pharmaceutical composition comprising the antibody, or antigen-binding portion thereof, of claim 1, and a pharmaceutically acceptable carrier.

11. The pharmaceutical composition of claim 10, further comprising an anti-tumor agent.

12. A method for treating a cancer disease in a subject, comprising administering to the subject a therapeutically effective amount of the pharmaceutical composition of claim 10.

13. The method of claim 12, wherein the cancer disease is selected from the group consisting of pancreatic cancer, gastric cancer, colon cancer, esophageal cancer, hepatic cancer, ovarian cancer, lung cancer and bladder cancer.

14. The method of claim 12, further comprising administering an immunostimulatory antibody, a costimulatory antibody, a chemotherapeutic agent, an agent stimulating γδ T cells and/or an agent stabilizing or increasing expression of Claudin 18.2.

15. The method of claim 14, wherein the immunostimulatory antibody is selected from the group consisting of an anti-PD-1 antibody, an anti-PD-L1 antibody, an anti-LAG-3 antibody, an anti-TIM 3 antibody, an anti-STAT3 antibody, and an anti-ROR1 antibody.

16. The method of claim 14, wherein the costimulatory antibody is an anti-CD137 antibody or an anti-GITR antibody.

17. The method of claim 14, wherein the chemotherapeutic agent is epitubicin, oxaliplatin, and/or 5-fluorouracil.

18. The method of claim 14, wherein the agent stimulating γδ T cells is zoledronic acid.

19. The method of claim 14, wherein the agent stabilizing or increasing expression of Claudin 18.2 comprises (i) epirubicin, oxaliplatin and 5-fluorouracil, (ii) epirubicin, oxaliplatin and capecitabine, (iii) epirubicin, cisplatin and 5-fluorouracil, (iv) epirubicin, cisplatin and capecitabine, or (v) folinic acid, oxaliplatin and 5-fluorouracil.

* * * * *